United States Patent
Diedering et al.

(10) Patent No.: US 11,931,253 B2
(45) Date of Patent: Mar. 19, 2024

(54) PROSTHETIC HEART VALVE DELIVERY SYSTEM: BALL-SLIDE ATTACHMENT

(71) Applicant: 4C Medical Technologies, Inc., Maple Grove, MN (US)

(72) Inventors: Jason S. Diedering, Minneapolis, MN (US); Thomas Benson, Maple Grove, MN (US)

(73) Assignee: 4C Medical Technologies, Inc., Maple Grove, MN (US)

( * ) Notice: Subject to any disclaimer, the term of this patent is extended or adjusted under 35 U.S.C. 154(b) by 165 days.

(21) Appl. No.: 17/158,475

(22) Filed: Jan. 26, 2021

(65) Prior Publication Data

US 2021/0236276 A1 Aug. 5, 2021

Related U.S. Application Data

(60) Provisional application No. 62/968,216, filed on Jan. 31, 2020.

(51) Int. Cl.
*A61F 2/24* (2006.01)
*A61F 2/966* (2013.01)

(52) U.S. Cl.
CPC .......... *A61F 2/2418* (2013.01); *A61F 2/2433* (2013.01); *A61F 2/2436* (2013.01); *A61F 2/966* (2013.01)

(58) Field of Classification Search
CPC .............. A61F 2/24–2496; A61F 2/966; A61F 2/2418; A61F 2/2433; A61F 2/2436; A61F 2/2966
See application file for complete search history.

(56) References Cited

U.S. PATENT DOCUMENTS

| | | |
|---|---|---|
| 4,424,833 A | 1/1984 | Spector |
| 4,503,569 A | 3/1985 | Dotter |
| 4,733,665 A | 3/1988 | Palmaz |
| 4,878,906 A | 11/1989 | Lindemann |
| 5,190,528 A | 3/1993 | Fonger |
| 5,415,667 A | 5/1995 | Frater |
| 5,441,483 A | 8/1995 | Avitall |

(Continued)

FOREIGN PATENT DOCUMENTS

| | | |
|---|---|---|
| AU | 2014203064 B2 | 6/2015 |
| AU | 2015230879 A1 | 10/2015 |

(Continued)

OTHER PUBLICATIONS

International Search Report and Written Opinion issued in PCT/US2021/015387, dated Jun. 3, 2021.

(Continued)

*Primary Examiner* — Alexander J Orkin
(74) *Attorney, Agent, or Firm* — Weiss & Arons LLP

(57) ABSTRACT

Systems, devices and methods for attaching an operator-manipulatable tether(s) to the stent for: loading and/or collapsing the expandable stent into a delivery catheter or sheath, translating the collapsed stent along the delivery catheter or sheath, delivering the expandable stent into the subject heart chamber, repositioning the expandable stent as necessary within the subject heart chamber, recapturing or resheathing the expandable stent within the delivery catheter or sheath if needed, and deploying the expandable stent to, and within, the subject heart chamber.

15 Claims, 7 Drawing Sheets

(56) References Cited

U.S. PATENT DOCUMENTS

| | | | |
|---|---|---|---|
| 5,693,083 | A | 12/1997 | Baker |
| 5,693,089 | A | 12/1997 | Inoue |
| 5,776,188 | A | 7/1998 | Shepherd |
| 5,843,090 | A | 12/1998 | Schuetz |
| 5,928,258 | A | 7/1999 | Khan |
| 5,957,949 | A | 9/1999 | Leonhardt |
| 5,968,070 | A | 10/1999 | Bley |
| 6,123,723 | A | 9/2000 | Konya |
| 6,152,144 | A | 11/2000 | Lesh |
| 6,231,602 | B1 | 5/2001 | Carpentier |
| 6,287,334 | B1 | 9/2001 | Moll |
| 6,319,280 | B1 | 11/2001 | Schoon |
| 6,319,281 | B1 | 11/2001 | Patel |
| 6,332,893 | B1 | 12/2001 | Mortier |
| 6,371,983 | B1 | 4/2002 | Lane |
| 6,409,758 | B2 | 6/2002 | Stobie |
| 6,425,916 | B1 | 7/2002 | Garrison |
| 6,471,718 | B1 | 10/2002 | Staehle |
| 6,494,909 | B2 | 12/2002 | Greenhalgh |
| 6,503,272 | B2 | 1/2003 | Duerig |
| 6,540,782 | B1 | 4/2003 | Snyders |
| 6,569,196 | B1 | 5/2003 | Vesely |
| 6,589,275 | B1 | 7/2003 | Ivancev |
| 6,702,826 | B2 | 3/2004 | Liddicoat |
| 6,738,655 | B1 | 5/2004 | Sen |
| 6,790,231 | B2 | 9/2004 | Liddicoat |
| 6,790,237 | B2 | 9/2004 | Stinson |
| 6,821,297 | B2 | 11/2004 | Snyders |
| 6,830,585 | B1 | 12/2004 | Artof |
| 6,840,957 | B2 | 1/2005 | Dimatteo |
| 6,875,231 | B2 | 4/2005 | Anduiza |
| 6,908,481 | B2 * | 6/2005 | Cribier ................ A61F 2/2418 623/2.11 |
| 7,011,671 | B2 | 3/2006 | Welch |
| 7,041,132 | B2 | 5/2006 | Quijano |
| 7,044,966 | B2 | 5/2006 | Svanidze |
| 7,125,420 | B2 | 10/2006 | Rourke |
| 7,153,324 | B2 | 12/2006 | Case |
| 7,252,682 | B2 | 8/2007 | Seguin |
| 7,276,077 | B2 | 10/2007 | Zadno-Azizi |
| 7,276,078 | B2 | 10/2007 | Spenser |
| 7,291,168 | B2 | 11/2007 | Macoviak |
| 7,364,588 | B2 | 4/2008 | Mathis |
| 7,381,220 | B2 | 6/2008 | Macoviak |
| 7,442,204 | B2 | 10/2008 | Schwammenthal |
| 7,445,631 | B2 | 11/2008 | Salahieh |
| 7,455,689 | B2 | 11/2008 | Johnson |
| 7,510,572 | B2 | 3/2009 | Gabbay |
| 7,524,331 | B2 | 4/2009 | Birdsall |
| 7,611,534 | B2 | 11/2009 | Kapadia |
| 7,704,277 | B2 | 4/2010 | Zakay |
| 7,749,266 | B2 | 7/2010 | Forster |
| 7,758,491 | B2 | 7/2010 | Buckner |
| 7,780,723 | B2 | 8/2010 | Taylor |
| 7,789,909 | B2 | 9/2010 | Andersen |
| 7,935,144 | B2 | 5/2011 | Robin |
| 7,959,672 | B2 | 6/2011 | Salahieh |
| 7,967,853 | B2 | 6/2011 | Eidenschink |
| 7,998,196 | B2 | 8/2011 | Mathison |
| 8,012,201 | B2 | 9/2011 | Lashinski |
| 8,016,877 | B2 | 9/2011 | Seguin |
| 8,021,420 | B2 | 9/2011 | Dolan |
| 8,029,556 | B2 | 10/2011 | Rowe |
| D648,854 | S | 11/2011 | Braido |
| 8,052,592 | B2 | 11/2011 | Goldfarb |
| 8,057,493 | B2 | 11/2011 | Goldfarb |
| 8,070,802 | B2 | 12/2011 | Lamphere |
| 8,083,793 | B2 | 12/2011 | Lane |
| D653,341 | S | 1/2012 | Braido |
| D653,342 | S | 1/2012 | Braido |
| 8,092,524 | B2 | 1/2012 | Nugent |
| 8,142,492 | B2 | 3/2012 | Forster |
| 8,147,541 | B2 | 4/2012 | Forster |
| D660,433 | S | 5/2012 | Braido |
| D660,967 | S | 5/2012 | Braido |
| 8,167,932 | B2 | 5/2012 | Bourang |
| 8,236,049 | B2 | 8/2012 | Rowe |
| 8,246,677 | B2 | 8/2012 | Ryan |
| 8,252,051 | B2 | 8/2012 | Chau |
| 8,287,538 | B2 | 10/2012 | Brenzel et al. |
| 8,308,798 | B2 | 11/2012 | Pintor |
| 8,313,525 | B2 | 11/2012 | Tuval et al. |
| 8,348,998 | B2 | 1/2013 | Pintor |
| 8,348,999 | B2 | 1/2013 | Kheradvar |
| 8,366,768 | B2 | 2/2013 | Zhang |
| 8,398,708 | B2 | 3/2013 | Meiri |
| 8,409,275 | B2 | 4/2013 | Matheny |
| 8,414,644 | B2 | 4/2013 | Quadri |
| 8,414,645 | B2 | 4/2013 | Dwork |
| 8,439,970 | B2 | 5/2013 | Jimenez |
| 8,454,686 | B2 | 6/2013 | Alkhatib |
| 8,465,541 | B2 | 6/2013 | Dwork |
| 8,491,650 | B2 | 7/2013 | Wiemeyer |
| 8,512,400 | B2 | 8/2013 | Tran |
| 8,518,106 | B2 | 8/2013 | Duffy |
| 8,535,373 | B2 | 9/2013 | Stacchino |
| 8,562,673 | B2 | 10/2013 | Yeung |
| 8,568,472 | B2 | 10/2013 | Marchand |
| 8,579,963 | B2 | 11/2013 | Tabor |
| 8,579,964 | B2 | 11/2013 | Lane |
| 8,603,159 | B2 | 12/2013 | Seguin |
| 8,623,075 | B2 | 1/2014 | Murray, III |
| 8,636,764 | B2 | 1/2014 | Miles |
| 8,641,757 | B2 | 2/2014 | Pintor |
| 8,657,870 | B2 | 2/2014 | Turovskiy |
| 8,663,318 | B2 | 3/2014 | Ho |
| 8,679,176 | B2 | 3/2014 | Matheny |
| 8,721,715 | B2 | 5/2014 | Wang |
| 8,740,976 | B2 | 6/2014 | Tran |
| 8,747,459 | B2 | 6/2014 | Nguyen |
| 8,747,461 | B2 | 6/2014 | Centola |
| 8,764,793 | B2 | 7/2014 | Lee |
| 8,764,820 | B2 | 7/2014 | Dehdashtian |
| 8,778,020 | B2 | 7/2014 | Gregg |
| 8,790,396 | B2 | 7/2014 | Bergheim |
| 8,795,354 | B2 | 8/2014 | Benichou |
| 8,795,357 | B2 | 8/2014 | Yohanan |
| 8,805,466 | B2 | 8/2014 | Salahieh |
| 8,814,931 | B2 | 8/2014 | Wang |
| 8,828,043 | B2 | 9/2014 | Chambers |
| 8,828,051 | B2 | 9/2014 | Javois |
| 8,845,711 | B2 | 9/2014 | Miles |
| 8,845,722 | B2 | 9/2014 | Gabbay |
| 8,852,271 | B2 | 10/2014 | Murray, III |
| 8,852,272 | B2 | 10/2014 | Gross |
| 8,870,949 | B2 | 10/2014 | Rowe |
| 8,876,897 | B2 | 11/2014 | Kheradvar |
| 8,906,022 | B2 | 12/2014 | Krinke et al. |
| 8,926,692 | B2 | 1/2015 | Dwork |
| 8,956,402 | B2 | 2/2015 | Cohn |
| 8,956,405 | B2 | 2/2015 | Wang |
| 8,961,518 | B2 | 2/2015 | Kyle et al. |
| 8,986,372 | B2 | 3/2015 | Murry, III |
| 8,986,374 | B2 | 3/2015 | Cao |
| 8,986,375 | B2 | 3/2015 | Garde |
| 8,998,980 | B2 | 4/2015 | Shipley |
| 8,998,982 | B2 | 4/2015 | Richter |
| 9,005,273 | B2 | 4/2015 | Salahieh |
| 9,011,527 | B2 | 4/2015 | Li |
| D730,520 | S | 5/2015 | Braido |
| D730,521 | S | 5/2015 | Braido |
| 9,023,101 | B2 | 5/2015 | Krahbichler |
| 9,050,188 | B2 | 6/2015 | Schweich, Jr. |
| 9,060,855 | B2 | 6/2015 | Tuval |
| 9,060,857 | B2 | 6/2015 | Nguyen |
| 9,060,858 | B2 | 6/2015 | Thornton |
| 9,061,119 | B2 | 6/2015 | Le |
| 9,066,800 | B2 | 6/2015 | Clague |
| 9,072,603 | B2 | 7/2015 | Tuval |
| 9,101,471 | B2 | 8/2015 | Kleinschrodt |
| 9,119,717 | B2 | 9/2015 | Wang |
| 9,132,008 | B2 | 9/2015 | Dwork |
| 9,132,009 | B2 | 9/2015 | Hacohen |
| 9,138,313 | B2 | 9/2015 | McGuckin, Jr. |

(56) References Cited

U.S. PATENT DOCUMENTS

| | | |
|---|---|---|
| 9,144,493 B2 | 9/2015 | Carr |
| 9,144,494 B2 | 9/2015 | Murray |
| 9,155,619 B2 | 10/2015 | Liu |
| 9,161,835 B2 | 10/2015 | Rankin |
| 9,173,737 B2 | 11/2015 | Hill |
| 9,192,466 B2 | 11/2015 | Kovalsky |
| 9,226,820 B2 | 1/2016 | Braido |
| 9,232,942 B2 | 1/2016 | Seguin |
| 9,232,996 B2 | 1/2016 | Sun |
| 9,248,016 B2 | 2/2016 | Oba |
| 9,259,315 B2 | 2/2016 | Zhou |
| 9,271,856 B2 | 3/2016 | Duffy |
| 9,277,993 B2 | 3/2016 | Gamarra |
| 9,289,289 B2 | 3/2016 | Rolando |
| 9,289,292 B2 | 3/2016 | Anderl |
| 9,295,547 B2 | 3/2016 | Costello |
| 9,295,549 B2 | 3/2016 | Braido |
| 9,301,836 B2 | 4/2016 | Buchbinder |
| 9,301,839 B2 | 4/2016 | Stante |
| 9,320,597 B2 | 4/2016 | Savage |
| 9,320,599 B2 | 4/2016 | Salahieh |
| 9,326,853 B2 | 5/2016 | Olson |
| 9,326,854 B2 | 5/2016 | Casley |
| 9,333,075 B2 | 5/2016 | Biadillah |
| 9,345,572 B2 | 5/2016 | Cerf |
| 9,351,831 B2 | 5/2016 | Braido |
| 9,358,108 B2 | 6/2016 | Bortlein |
| 9,364,325 B2 | 6/2016 | Alon |
| 9,364,637 B2 | 6/2016 | Rothstein |
| 9,370,422 B2 | 6/2016 | Wang |
| 9,387,106 B2 | 7/2016 | Stante |
| 9,402,720 B2 | 8/2016 | Richter |
| 9,414,910 B2 | 8/2016 | Lim |
| 9,414,917 B2 | 8/2016 | Young |
| 9,427,316 B2 | 8/2016 | Schweich, Jr. |
| 9,439,763 B2 | 9/2016 | Geist |
| 9,439,795 B2 | 9/2016 | Wang |
| 9,480,560 B2 | 11/2016 | Quadri |
| 9,498,370 B2 | 11/2016 | Kyle et al. |
| 9,504,569 B2 | 11/2016 | Malewicz |
| 9,522,062 B2 | 12/2016 | Tuval |
| 9,566,152 B2 | 2/2017 | Schweich, Jr. |
| 9,579,194 B2 | 2/2017 | Elizondo |
| 9,579,197 B2 | 2/2017 | Duffy |
| 9,622,863 B2 | 4/2017 | Karapetian |
| 9,717,592 B2 | 8/2017 | Thapliyal |
| 9,730,791 B2 | 8/2017 | Ratz |
| 9,737,400 B2 | 8/2017 | Fish |
| 9,737,401 B2 | 8/2017 | Conklin |
| 9,750,604 B2 | 9/2017 | Naor |
| 9,763,780 B2 | 9/2017 | Morriss |
| 9,795,477 B2 | 10/2017 | Tran |
| 9,801,711 B2 | 10/2017 | Gainor |
| 9,827,093 B2 | 11/2017 | Cartledge |
| 9,839,517 B2 | 12/2017 | Centola |
| 9,839,765 B2 | 12/2017 | Morris |
| 9,861,477 B2 | 1/2018 | Backus |
| 9,872,765 B2 | 1/2018 | Zeng |
| 9,877,830 B2 | 1/2018 | Lim |
| 9,968,443 B2 | 5/2018 | Bruchman |
| 10,004,601 B2 | 6/2018 | Tuval |
| 10,016,274 B2 | 7/2018 | Tabor |
| 10,016,275 B2 | 7/2018 | Nyuli |
| 10,022,132 B2 | 7/2018 | Wlodarski et al. |
| 10,034,750 B2 | 7/2018 | Morriss |
| 10,039,637 B2 | 8/2018 | Maimon |
| 10,039,642 B2 | 8/2018 | Hillukka |
| 10,098,735 B2 | 10/2018 | Lei |
| 10,098,763 B2 | 10/2018 | Lei |
| 10,117,742 B2 | 11/2018 | Braido |
| 10,143,551 B2 | 12/2018 | Braido |
| 10,182,907 B2 | 1/2019 | Lapeyre |
| 10,195,023 B2 | 2/2019 | Wrobel |
| 10,226,340 B2 | 3/2019 | Keren |
| 10,231,834 B2 | 3/2019 | Keidar |
| 10,238,490 B2 | 3/2019 | Gifford, III |
| 10,245,145 B2 | 4/2019 | Mantanus |
| 10,258,464 B2 | 4/2019 | Delaloye |
| 10,299,917 B2 | 5/2019 | Morriss |
| 10,321,990 B2 | 6/2019 | Braido |
| 10,327,892 B2 | 6/2019 | O'Connor |
| 10,327,893 B2 | 6/2019 | Maiorano |
| 10,350,065 B2 | 7/2019 | Quadri |
| 10,357,360 B2 | 7/2019 | Hariton |
| 10,368,982 B2 | 8/2019 | Weber |
| 10,376,363 B2 | 8/2019 | Quadri |
| 10,383,725 B2 | 8/2019 | Chambers |
| 10,390,943 B2 | 8/2019 | Hernandez |
| 10,405,974 B2 | 9/2019 | Hayes |
| 10,433,961 B2 | 10/2019 | McLean |
| 10,470,880 B2 | 11/2019 | Braido |
| 10,492,907 B2 | 12/2019 | Duffy |
| 10,500,041 B2 | 12/2019 | Valdez |
| 10,507,107 B2 | 12/2019 | Nathe |
| 10,512,537 B2 | 12/2019 | Corbett |
| 10,512,538 B2 | 12/2019 | Alkhatib |
| 10,517,726 B2 | 12/2019 | Chau |
| 10,524,902 B2 | 1/2020 | Gründeman |
| 10,524,910 B2 | 1/2020 | Hammer |
| 10,531,951 B2 | 1/2020 | Spargias |
| 10,537,427 B2 | 1/2020 | Zeng |
| 10,555,809 B2 | 2/2020 | Hastings |
| 10,555,812 B2 | 2/2020 | Duffy |
| 10,561,495 B2 | 2/2020 | Chambers |
| 10,595,992 B2 | 3/2020 | Chambers |
| 10,610,362 B2 | 4/2020 | Quadri |
| 10,653,523 B2 | 5/2020 | Chambers |
| 10,667,905 B2 | 6/2020 | Ekvall |
| 10,667,909 B2 | 6/2020 | Richter |
| 10,702,379 B2 | 7/2020 | Garde |
| 10,702,380 B2 | 7/2020 | Morriss |
| 10,709,560 B2 | 7/2020 | Kofidis |
| 10,751,169 B2 | 8/2020 | Chambers |
| 10,751,170 B2 | 8/2020 | Richter |
| 10,751,172 B2 | 8/2020 | Para |
| 10,758,265 B2 | 9/2020 | Siegel |
| 10,758,342 B2 | 9/2020 | Chau |
| 10,779,935 B2 | 9/2020 | Scorsin |
| 10,779,936 B2 | 9/2020 | Pollak |
| 10,779,968 B2 | 9/2020 | Giasolli |
| 10,786,351 B2 | 9/2020 | Christianson |
| 10,828,152 B2 | 11/2020 | Chambers |
| 10,856,983 B2 | 12/2020 | Keränen |
| 10,869,756 B2 | 12/2020 | Al-Jilaihawi |
| 10,874,513 B2 * | 12/2020 | Chambers ............... A61F 2/243 |
| 10,945,835 B2 | 3/2021 | Morriss |
| 10,973,630 B2 | 4/2021 | Torrianni |
| 10,980,636 B2 | 4/2021 | Delaloye |
| 11,000,000 B2 | 5/2021 | Diedering |
| 11,007,053 B2 | 5/2021 | Braido |
| 11,007,054 B2 | 5/2021 | Braido |
| 11,013,599 B2 | 5/2021 | Subramanian |
| 11,026,782 B2 | 6/2021 | Chambers |
| 11,026,788 B2 | 6/2021 | Metchik et al. |
| 11,033,275 B2 | 6/2021 | Franano et al. |
| 11,045,202 B2 | 6/2021 | Amplatz |
| 11,065,113 B2 | 7/2021 | Backus |
| 11,065,116 B2 | 7/2021 | Tegels |
| 11,065,138 B2 | 7/2021 | Schreck |
| 11,096,781 B2 | 8/2021 | Gurovich |
| 11,147,666 B2 | 10/2021 | Braido |
| 11,154,239 B2 | 10/2021 | Toth |
| 11,154,396 B2 | 10/2021 | Dibie |
| 11,154,398 B2 | 10/2021 | Straubinger |
| 11,197,754 B2 | 12/2021 | Saffari |
| 11,207,176 B2 | 12/2021 | Delaloye |
| 11,278,399 B2 | 3/2022 | Liu |
| 11,278,406 B2 | 3/2022 | Straubinger |
| 11,351,028 B2 | 6/2022 | Peterson |
| 11,389,293 B2 | 7/2022 | Torrianni |
| 11,395,734 B2 | 7/2022 | Lee |
| 11,413,141 B2 | 8/2022 | Morin |
| 11,419,716 B2 | 8/2022 | Braido |
| 11,452,628 B2 | 9/2022 | Diedering |

(56) References Cited

U.S. PATENT DOCUMENTS

| | | |
|---|---|---|
| 11,458,013 B2 | 10/2022 | Righini |
| 2001/0005787 A1 | 6/2001 | Oz |
| 2002/0072710 A1 | 6/2002 | Stewart |
| 2002/0161377 A1 | 10/2002 | Rabkin |
| 2003/0057156 A1 | 3/2003 | Peterson |
| 2003/0083730 A1 | 5/2003 | Stinson |
| 2003/0199971 A1 | 10/2003 | Tower |
| 2003/0225445 A1 | 12/2003 | Derus |
| 2003/0233141 A1 | 12/2003 | Israel |
| 2004/0073286 A1 | 4/2004 | Armstrong |
| 2004/0088041 A1 | 5/2004 | Stanford |
| 2004/0210307 A1 | 10/2004 | Khairkhahan |
| 2004/0243107 A1 | 12/2004 | Macoviak |
| 2005/0004641 A1 | 1/2005 | Pappu |
| 2005/0075727 A1 | 4/2005 | Wheatley |
| 2005/0096739 A1 | 5/2005 | Cao |
| 2005/0113861 A1 | 5/2005 | Corcoran |
| 2005/0197694 A1 | 9/2005 | Pai |
| 2005/0273160 A1 | 12/2005 | Lashinski |
| 2006/0142847 A1 | 6/2006 | Shaknovich |
| 2006/0184226 A1 | 8/2006 | Austin |
| 2006/0224183 A1 | 10/2006 | Freudenthal |
| 2006/0229708 A1 | 10/2006 | Powell |
| 2006/0271173 A1 | 11/2006 | Delgado |
| 2006/0276874 A1 | 12/2006 | Wilson |
| 2007/0016288 A1* | 1/2007 | Gurskis ............... A61F 2/2418 623/2.11 |
| 2007/0173930 A1 | 7/2007 | Sogard |
| 2007/0233223 A1 | 10/2007 | Styrc |
| 2007/0238979 A1 | 10/2007 | Huynh |
| 2007/0239254 A1 | 10/2007 | Chia |
| 2007/0239271 A1 | 10/2007 | Nguyen |
| 2007/0270931 A1 | 11/2007 | Leanna |
| 2007/0275027 A1 | 11/2007 | Wen et al. |
| 2007/0293942 A1 | 12/2007 | Mirzaee |
| 2008/0039928 A1 | 2/2008 | Peacock |
| 2008/0082166 A1* | 4/2008 | Styrc ............... A61F 2/2418 623/2.18 |
| 2008/0262592 A1 | 10/2008 | Jordan |
| 2008/0269877 A1 | 10/2008 | Jenson |
| 2008/0275540 A1 | 11/2008 | Wen |
| 2008/0281398 A1 | 11/2008 | Koss |
| 2008/0288042 A1 | 11/2008 | Purdy |
| 2008/0288055 A1 | 11/2008 | Paul, Jr. |
| 2009/0076585 A1 | 3/2009 | Hendriksen |
| 2009/0082840 A1 | 3/2009 | Rusk |
| 2009/0099640 A1 | 4/2009 | Weng |
| 2009/0099647 A1 | 4/2009 | Glimsdale |
| 2009/0125096 A1 | 5/2009 | Chu |
| 2009/0143852 A1 | 6/2009 | Chambers |
| 2009/0171447 A1 | 7/2009 | Von Segesser |
| 2009/0171456 A1 | 7/2009 | Kveen |
| 2009/0198315 A1 | 8/2009 | Boudjemline |
| 2009/0248134 A1 | 10/2009 | Dierking |
| 2009/0248143 A1 | 10/2009 | Laham |
| 2009/0270967 A1 | 10/2009 | Fleming, III |
| 2009/0276039 A1 | 11/2009 | Meretei |
| 2009/0281609 A1 | 11/2009 | Benichou |
| 2010/0021726 A1 | 1/2010 | Jo |
| 2010/0049313 A1 | 2/2010 | Alon et al. |
| 2010/0057192 A1 | 3/2010 | Celermajer |
| 2010/0069948 A1 | 3/2010 | Veznedaroglu |
| 2010/0168839 A1 | 7/2010 | Braido |
| 2010/0174355 A1 | 7/2010 | Boyle |
| 2010/0217260 A1 | 8/2010 | Aramayo |
| 2010/0217261 A1 | 8/2010 | Watson |
| 2010/0217262 A1 | 8/2010 | Stevenson |
| 2010/0217263 A1 | 8/2010 | Tukulj-Popovic |
| 2010/0217264 A1 | 8/2010 | Odom |
| 2010/0217265 A1 | 8/2010 | Chen |
| 2010/0217266 A1 | 8/2010 | Helevirta |
| 2010/0217267 A1 | 8/2010 | Bergin |
| 2010/0217268 A1 | 8/2010 | Bloebaum |
| 2010/0217269 A1 | 8/2010 | Landes |
| 2010/0256749 A1 | 10/2010 | Tran |
| 2010/0262157 A1 | 10/2010 | Silver |
| 2011/0022151 A1 | 1/2011 | Shin |
| 2011/0046712 A1 | 2/2011 | Melsheimer |
| 2011/0082539 A1 | 4/2011 | Suri |
| 2011/0082540 A1 | 4/2011 | Forster |
| 2011/0208293 A1 | 8/2011 | Tabor |
| 2011/0218585 A1 | 9/2011 | Krinke et al. |
| 2011/0251676 A1 | 10/2011 | Sweeney |
| 2011/0269051 A1 | 11/2011 | Wijenberg |
| 2011/0301702 A1 | 12/2011 | Rust |
| 2011/0319988 A1 | 12/2011 | Schankereli |
| 2011/0319991 A1 | 12/2011 | Hariton |
| 2012/0016468 A1 | 1/2012 | Robin |
| 2012/0035719 A1 | 2/2012 | Forster |
| 2012/0078356 A1 | 3/2012 | Fish |
| 2012/0083875 A1 | 4/2012 | Johnson |
| 2012/0095551 A1 | 4/2012 | Navia |
| 2012/0101567 A1 | 4/2012 | Jansen |
| 2012/0101571 A1 | 4/2012 | Thambar |
| 2012/0109079 A1 | 5/2012 | Asleson |
| 2012/0197390 A1* | 8/2012 | Alkhatib ............... A61F 2/2418 623/2.18 |
| 2012/0209375 A1 | 8/2012 | Madrid |
| 2012/0226130 A1 | 9/2012 | De Graff |
| 2012/0303048 A1 | 11/2012 | Manasse |
| 2012/0323313 A1 | 12/2012 | Seguin |
| 2013/0023852 A1 | 1/2013 | Drasler |
| 2013/0060329 A1 | 3/2013 | Agnew |
| 2013/0066419 A1 | 3/2013 | Gregg |
| 2013/0079872 A1 | 3/2013 | Gallagher |
| 2013/0090728 A1 | 4/2013 | Solem |
| 2013/0096671 A1 | 4/2013 | Iobbi |
| 2013/0123911 A1 | 5/2013 | Chalekian |
| 2013/0138138 A1 | 5/2013 | Clark |
| 2013/0150956 A1 | 6/2013 | Yohanan |
| 2013/0184811 A1 | 7/2013 | Rowe |
| 2013/0190861 A1 | 7/2013 | Chau |
| 2013/0204311 A1 | 8/2013 | Kunis |
| 2013/0204360 A1 | 8/2013 | Gainor |
| 2013/0226286 A1 | 8/2013 | Hargreaves |
| 2013/0231736 A1 | 9/2013 | Essinger |
| 2013/0238089 A1 | 9/2013 | Lichtenstein |
| 2013/0297010 A1 | 11/2013 | Bishop |
| 2013/0297012 A1 | 11/2013 | Willard |
| 2013/0304197 A1 | 11/2013 | Buchbinder |
| 2013/0310917 A1 | 11/2013 | Richter |
| 2013/0310923 A1 | 11/2013 | Kheradvar |
| 2013/0317598 A1 | 11/2013 | Rowe |
| 2013/0317603 A1* | 11/2013 | McLean ............... A61F 2/2427 623/2.12 |
| 2013/0331933 A1 | 12/2013 | Alkhatib |
| 2014/0005768 A1 | 1/2014 | Thomas |
| 2014/0005773 A1 | 1/2014 | Wheatley |
| 2014/0005778 A1 | 1/2014 | Buchbinder |
| 2014/0012371 A1 | 1/2014 | Li |
| 2014/0018841 A1 | 1/2014 | Peiffer |
| 2014/0018906 A1 | 1/2014 | Rafiee |
| 2014/0031928 A1 | 1/2014 | Murphy |
| 2014/0031951 A1 | 1/2014 | Costello |
| 2014/0039613 A1 | 2/2014 | Navia |
| 2014/0046433 A1 | 2/2014 | Kovalsky |
| 2014/0046436 A1 | 2/2014 | Kheradvar |
| 2014/0052238 A1 | 2/2014 | Wang |
| 2014/0052241 A1 | 2/2014 | Harks |
| 2014/0057730 A1 | 2/2014 | Steinhauser |
| 2014/0057731 A1 | 2/2014 | Stephens |
| 2014/0057732 A1 | 2/2014 | Gilbert |
| 2014/0057733 A1 | 2/2014 | Yamamoto |
| 2014/0057734 A1 | 2/2014 | Lu |
| 2014/0057735 A1 | 2/2014 | Yu |
| 2014/0057736 A1 | 2/2014 | Burnett |
| 2014/0057737 A1 | 2/2014 | Solheim |
| 2014/0057738 A1 | 2/2014 | Albertsen |
| 2014/0057739 A1 | 2/2014 | Stites |
| 2014/0067050 A1 | 3/2014 | Costello |
| 2014/0074151 A1 | 3/2014 | Tischler |
| 2014/0081308 A1 | 3/2014 | Wondka |
| 2014/0081375 A1 | 3/2014 | Bardill et al. |
| 2014/0088696 A1 | 3/2014 | Figulla |

(56) References Cited

U.S. PATENT DOCUMENTS

| | | | |
|---|---|---|---|
| 2014/0114340 A1 | 4/2014 | Zhou | |
| 2014/0128963 A1 | 5/2014 | Quill | |
| 2014/0134322 A1 | 5/2014 | Larsen | |
| 2014/0135817 A1 | 5/2014 | Tischler | |
| 2014/0135907 A1 | 5/2014 | Gallagher | |
| 2014/0142612 A1 | 5/2014 | Li | |
| 2014/0142680 A1 | 5/2014 | Laske | |
| 2014/0142688 A1 | 5/2014 | Duffy | |
| 2014/0142691 A1 | 5/2014 | Pouletty | |
| 2014/0163668 A1* | 6/2014 | Rafiee | A61F 2/2439 623/2.11 |
| 2014/0172076 A1 | 6/2014 | Jonsson | |
| 2014/0172083 A1 | 6/2014 | Bruchman | |
| 2014/0180397 A1 | 6/2014 | Gerberding | |
| 2014/0180401 A1 | 6/2014 | Quill | |
| 2014/0188157 A1 | 7/2014 | Clark | |
| 2014/0194979 A1 | 7/2014 | Seguin | |
| 2014/0194983 A1* | 7/2014 | Kovalsky | A61F 2/2445 623/2.38 |
| 2014/0222140 A1 | 8/2014 | Schreck | |
| 2014/0228944 A1 | 8/2014 | Paniagua | |
| 2014/0236288 A1 | 8/2014 | Lambrecht | |
| 2014/0243954 A1 | 8/2014 | Shannon | |
| 2014/0243967 A1 | 8/2014 | Salahieh | |
| 2014/0243969 A1 | 8/2014 | Venkatasubramani | |
| 2014/0249564 A1 | 9/2014 | Daly | |
| 2014/0249621 A1 | 9/2014 | Eidenschink | |
| 2014/0257467 A1 | 9/2014 | Lane | |
| 2014/0276395 A1 | 9/2014 | Wilson | |
| 2014/0277074 A1 | 9/2014 | Kaplan | |
| 2014/0277119 A1 | 9/2014 | Akpinar | |
| 2014/0277388 A1 | 9/2014 | Skemp | |
| 2014/0277389 A1* | 9/2014 | Braido | A61F 2/2418 623/1.26 |
| 2014/0277408 A1 | 9/2014 | Folan | |
| 2014/0277411 A1 | 9/2014 | Börtlein | |
| 2014/0277417 A1 | 9/2014 | Schraut | |
| 2014/0277422 A1 | 9/2014 | Ratz | |
| 2014/0277424 A1 | 9/2014 | Oslund | |
| 2014/0277425 A1 | 9/2014 | Dakin | |
| 2014/0277426 A1 | 9/2014 | Dakin | |
| 2014/0288634 A1 | 9/2014 | Shalev | |
| 2014/0288639 A1 | 9/2014 | Gainor | |
| 2014/0296909 A1 | 10/2014 | Heipl | |
| 2014/0296969 A1 | 10/2014 | Tegels | |
| 2014/0296970 A1 | 10/2014 | Ekvall | |
| 2014/0296975 A1 | 10/2014 | Tegels | |
| 2014/0309727 A1 | 10/2014 | Lamelas | |
| 2014/0330366 A1 | 11/2014 | Dehdashtian | |
| 2014/0330368 A1 | 11/2014 | Gloss | |
| 2014/0330369 A1 | 11/2014 | Matheny | |
| 2014/0330370 A1 | 11/2014 | Matheny | |
| 2014/0331475 A1 | 11/2014 | Duffy | |
| 2014/0343665 A1 | 11/2014 | Straubinger | |
| 2014/0343669 A1 | 11/2014 | Lane | |
| 2014/0343670 A1 | 11/2014 | Bakis | |
| 2014/0358224 A1 | 12/2014 | Tegels | |
| 2014/0371844 A1 | 12/2014 | Dale | |
| 2014/0379020 A1 | 12/2014 | Campbell | |
| 2015/0005857 A1 | 1/2015 | Kern | |
| 2015/0018933 A1 | 1/2015 | Yang | |
| 2015/0025621 A1 | 1/2015 | Costello | |
| 2015/0025625 A1 | 1/2015 | Rylski | |
| 2015/0039081 A1 | 2/2015 | Costello | |
| 2015/0039083 A1 | 2/2015 | Rafiee | |
| 2015/0066138 A1 | 3/2015 | Alexander | |
| 2015/0066141 A1 | 3/2015 | Braido | |
| 2015/0073548 A1 | 3/2015 | Matheny | |
| 2015/0088248 A1 | 3/2015 | Scorsin | |
| 2015/0088251 A1 | 3/2015 | May-Newman | |
| 2015/0094802 A1 | 4/2015 | Buchbinder | |
| 2015/0094804 A1 | 4/2015 | Bonhoeffer | |
| 2015/0112428 A1 | 4/2015 | Daly | |
| 2015/0112430 A1 | 4/2015 | Creaven | |
| 2015/0119974 A1 | 4/2015 | Rothstein | |
| 2015/0119978 A1 | 4/2015 | Tegels | |
| 2015/0119980 A1 | 4/2015 | Beith | |
| 2015/0119982 A1 | 4/2015 | Quill | |
| 2015/0127032 A1 | 5/2015 | Lentz | |
| 2015/0127093 A1* | 5/2015 | Hosmer | A61F 2/2418 623/2.11 |
| 2015/0127097 A1 | 5/2015 | Neumann | |
| 2015/0127100 A1 | 5/2015 | Braido | |
| 2015/0134054 A1 | 5/2015 | Morrissey | |
| 2015/0142100 A1* | 5/2015 | Morriss | A61F 2/246 623/2.4 |
| 2015/0142103 A1 | 5/2015 | Vidlund | |
| 2015/0142104 A1 | 5/2015 | Braido | |
| 2015/0148731 A1 | 5/2015 | McNamara | |
| 2015/0150678 A1 | 6/2015 | Brecker | |
| 2015/0157455 A1 | 6/2015 | Hoang | |
| 2015/0157458 A1 | 6/2015 | Thambar | |
| 2015/0173770 A1 | 6/2015 | Warner | |
| 2015/0173897 A1 | 6/2015 | Raanani | |
| 2015/0173898 A1 | 6/2015 | Drasler | |
| 2015/0173899 A1 | 6/2015 | Braido | |
| 2015/0196300 A1 | 7/2015 | Tischler | |
| 2015/0196390 A1 | 7/2015 | Ma | |
| 2015/0196393 A1 | 7/2015 | Vidlund | |
| 2015/0209140 A1 | 7/2015 | Bell | |
| 2015/0209143 A1 | 7/2015 | Duffy | |
| 2015/0223729 A1 | 8/2015 | Balachandran | |
| 2015/0223820 A1 | 8/2015 | Olson | |
| 2015/0223934 A1 | 8/2015 | Vidlund | |
| 2015/0230921 A1 | 8/2015 | Chau | |
| 2015/0238312 A1 | 8/2015 | Lashinski | |
| 2015/0238313 A1 | 8/2015 | Spence | |
| 2015/0257879 A1 | 9/2015 | Bortlein | |
| 2015/0257880 A1 | 9/2015 | Bortlein | |
| 2015/0257881 A1 | 9/2015 | Bortlein | |
| 2015/0257882 A1 | 9/2015 | Bortlein | |
| 2015/0265402 A1 | 9/2015 | Centola | |
| 2015/0265404 A1 | 9/2015 | Rankin | |
| 2015/0272730 A1 | 10/2015 | Melnick | |
| 2015/0272731 A1 | 10/2015 | Racchini | |
| 2015/0272737 A1* | 10/2015 | Dale | A61F 2/2442 623/2.37 |
| 2015/0272738 A1 | 10/2015 | Sievers | |
| 2015/0282931 A1 | 10/2015 | Brunnett | |
| 2015/0282958 A1 | 10/2015 | Centola | |
| 2015/0289972 A1 | 10/2015 | Yang | |
| 2015/0289974 A1 | 10/2015 | Matheny | |
| 2015/0289977 A1 | 10/2015 | Kovalsky | |
| 2015/0290007 A1 | 10/2015 | Aggerholm | |
| 2015/0297346 A1 | 10/2015 | Duffy | |
| 2015/0297381 A1 | 10/2015 | Essinger | |
| 2015/0305860 A1 | 10/2015 | Wang | |
| 2015/0305861 A1 | 10/2015 | Annest | |
| 2015/0313710 A1 | 11/2015 | Eberhardt | |
| 2015/0313712 A1 | 11/2015 | Carpentier | |
| 2015/0320552 A1 | 11/2015 | Letac | |
| 2015/0320556 A1 | 11/2015 | Levi | |
| 2015/0327995 A1* | 11/2015 | Morin | A61F 2/2436 623/2.17 |
| 2015/0327996 A1 | 11/2015 | Fahim | |
| 2015/0327999 A1 | 11/2015 | Board | |
| 2015/0328002 A1* | 11/2015 | McLean | A61F 2/2418 623/2.36 |
| 2015/0335422 A1 | 11/2015 | Straka | |
| 2015/0342718 A1 | 12/2015 | Weber | |
| 2015/0342734 A1 | 12/2015 | Braido | |
| 2015/0351735 A1 | 12/2015 | Keranen | |
| 2015/0351904 A1 | 12/2015 | Cooper | |
| 2015/0351905 A1* | 12/2015 | Khouengboua | A61F 2/2418 623/2.18 |
| 2015/0359628 A1 | 12/2015 | Keranen | |
| 2015/0359629 A1 | 12/2015 | Ganesan | |
| 2015/0366665 A1 | 12/2015 | Lombardi | |
| 2015/0366667 A1 | 12/2015 | Bailey | |
| 2015/0366690 A1 | 12/2015 | Lumauig | |
| 2015/0374490 A1 | 12/2015 | Alkhatib | |
| 2015/0374906 A1 | 12/2015 | Forsell | |
| 2016/0000559 A1 | 1/2016 | Chen | |
| 2016/0000562 A1 | 1/2016 | Siegel | |

(56) References Cited

U.S. PATENT DOCUMENTS

| | | |
|---|---|---|
| 2016/0008128 A1 | 1/2016 | Squara |
| 2016/0008131 A1 | 1/2016 | Christianson |
| 2016/0015512 A1 | 1/2016 | Zhang |
| 2016/0015515 A1 | 1/2016 | Lashinski |
| 2016/0022417 A1 | 1/2016 | Karapetian |
| 2016/0022418 A1 | 1/2016 | Salahieh |
| 2016/0030165 A1 | 2/2016 | Mitra |
| 2016/0030168 A1 | 2/2016 | Spenser |
| 2016/0030169 A1 | 2/2016 | Shahriari |
| 2016/0030170 A1 | 2/2016 | Alkhatib |
| 2016/0030171 A1 | 2/2016 | Quijano |
| 2016/0030173 A1 | 2/2016 | Cai |
| 2016/0030175 A1 | 2/2016 | Madjarov |
| 2016/0038283 A1 | 2/2016 | Divekar |
| 2016/0045306 A1 | 2/2016 | Agrawal |
| 2016/0045308 A1 | 2/2016 | Macoviak |
| 2016/0045309 A1 | 2/2016 | Valdez |
| 2016/0045310 A1 | 2/2016 | Alkhatib |
| 2016/0045311 A1 | 2/2016 | McCann |
| 2016/0051358 A1 | 2/2016 | Sutton |
| 2016/0051362 A1 | 2/2016 | Cooper |
| 2016/0051364 A1 | 2/2016 | Cunningham |
| 2016/0066922 A1 | 3/2016 | Bridgeman |
| 2016/0067038 A1 | 3/2016 | Park |
| 2016/0067041 A1 | 3/2016 | Alkhatib |
| 2016/0074161 A1 | 3/2016 | Bennett |
| 2016/0074164 A1 | 3/2016 | Naor |
| 2016/0074165 A1 | 3/2016 | Spence |
| 2016/0081799 A1 | 3/2016 | Leo |
| 2016/0089234 A1 | 3/2016 | Gifford, III |
| 2016/0089235 A1 | 3/2016 | Yellin |
| 2016/0089236 A1 | 3/2016 | Kovalsky |
| 2016/0095700 A1 | 4/2016 | Righini |
| 2016/0095701 A1 | 4/2016 | Dale |
| 2016/0095702 A1 | 4/2016 | Gainor |
| 2016/0095703 A1 | 4/2016 | Thomas |
| 2016/0095704 A1 | 4/2016 | Whitman |
| 2016/0100844 A1 | 4/2016 | Li |
| 2016/0100939 A1 | 4/2016 | Armstrong |
| 2016/0100941 A1 | 4/2016 | Czyscon |
| 2016/0100942 A1 | 4/2016 | Morrissey |
| 2016/0106539 A1 | 4/2016 | Buchbinder |
| 2016/0113764 A1 | 4/2016 | Sheahan |
| 2016/0113766 A1 | 4/2016 | Ganesan |
| 2016/0113767 A1 | 4/2016 | Miller |
| 2016/0113768 A1 | 4/2016 | Ganesan |
| 2016/0120642 A1 | 5/2016 | Shaolian |
| 2016/0120643 A1 | 5/2016 | Kupumbati |
| 2016/0120646 A1 | 5/2016 | Dwork |
| 2016/0135951 A1 | 5/2016 | Salahieh |
| 2016/0136412 A1 | 5/2016 | McKinnon |
| 2016/0143730 A1 | 5/2016 | Kheradvar |
| 2016/0143731 A1 | 5/2016 | Backus |
| 2016/0143734 A1 | 5/2016 | Shaolian |
| 2016/0151155 A1 | 6/2016 | Lutter |
| 2016/0157998 A1 | 6/2016 | Bruchman |
| 2016/0157999 A1 | 6/2016 | Lane |
| 2016/0158001 A1 | 6/2016 | Wallace |
| 2016/0158004 A1 | 6/2016 | Kumar |
| 2016/0158007 A1 | 6/2016 | Centola |
| 2016/0158011 A1 | 6/2016 | De Canniere |
| 2016/0158013 A1 | 6/2016 | Carpentier |
| 2016/0166381 A1 | 6/2016 | Sugimoto |
| 2016/0166382 A1 | 6/2016 | Nguyen |
| 2016/0166384 A1 | 6/2016 | Olson |
| 2016/0175096 A1 | 6/2016 | Dienno |
| 2016/0193044 A1 | 7/2016 | Achiluzzi |
| 2016/0193045 A1 | 7/2016 | Pollak |
| 2016/0193047 A1 | 7/2016 | Delaloye |
| 2016/0199177 A1 | 7/2016 | Spence |
| 2016/0199178 A1 | 7/2016 | Venkatasubramani |
| 2016/0199180 A1 | 7/2016 | Zeng |
| 2016/0199182 A1 | 7/2016 | Gorman, III |
| 2016/0213470 A1 | 7/2016 | Ahlberg |
| 2016/0220363 A1 | 8/2016 | Peter |
| 2016/0235525 A1 | 8/2016 | Rothstein |
| 2016/0235530 A1 | 8/2016 | Thomas |
| 2016/0235531 A1 | 8/2016 | Ciobanu |
| 2016/0250022 A1 | 9/2016 | Braido |
| 2016/0250051 A1 | 9/2016 | Lim |
| 2016/0256168 A1 | 9/2016 | Nielsen |
| 2016/0256270 A1 | 9/2016 | Folan |
| 2016/0262884 A1 | 9/2016 | Lombardi |
| 2016/0270910 A1 | 9/2016 | Birmingham |
| 2016/0270911 A1 | 9/2016 | Ganesan |
| 2016/0278922 A1* | 9/2016 | Braido .................. A61F 2/2418 |
| 2016/0296323 A1 | 10/2016 | Wulfman |
| 2016/0296333 A1 | 10/2016 | Balachandran |
| 2016/0302920 A1 | 10/2016 | Al-Jilaihawi |
| 2016/0302921 A1 | 10/2016 | Gosal |
| 2016/0302922 A1 | 10/2016 | Keidar |
| 2016/0310268 A1 | 10/2016 | Oba |
| 2016/0324640 A1 | 11/2016 | Gifford, III |
| 2016/0331527 A1* | 11/2016 | Vidlund ................ A61F 2/2409 |
| 2016/0331529 A1 | 11/2016 | Marchand |
| 2016/0346081 A1 | 12/2016 | Zeng |
| 2016/0354203 A1 | 12/2016 | Tuval et al. |
| 2016/0361161 A1* | 12/2016 | Braido .................. A61F 2/2409 |
| 2016/0374790 A1 | 12/2016 | Jacinto |
| 2016/0374801 A1 | 12/2016 | Jimenez |
| 2016/0374802 A1 | 12/2016 | Levi |
| 2016/0374803 A1 | 12/2016 | Figulla |
| 2016/0374842 A1 | 12/2016 | Havel |
| 2017/0079781 A1 | 3/2017 | Lim |
| 2017/0079785 A1 | 3/2017 | Li |
| 2017/0079787 A1 | 3/2017 | Benson |
| 2017/0079790 A1* | 3/2017 | Vidlund ............. A61B 17/0401 |
| 2017/0086973 A1 | 3/2017 | Zeng |
| 2017/0095256 A1 | 4/2017 | Lindgren |
| 2017/0100241 A1 | 4/2017 | Modine |
| 2017/0105839 A1 | 4/2017 | Subramanian |
| 2017/0165066 A1 | 6/2017 | Rothstein |
| 2017/0172737 A1 | 6/2017 | Kuetting |
| 2017/0202525 A1 | 7/2017 | Piazza |
| 2017/0252191 A1 | 9/2017 | Pacetti |
| 2017/0281193 A1 | 10/2017 | Asirvatham |
| 2017/0348098 A1 | 12/2017 | Rowe |
| 2017/0360570 A1 | 12/2017 | Berndt et al. |
| 2018/0014830 A1 | 1/2018 | Neumann |
| 2018/0055629 A1 | 3/2018 | Oba et al. |
| 2018/0092744 A1 | 4/2018 | Von Oepen |
| 2018/0116843 A1 | 5/2018 | Schreck |
| 2018/0116848 A1 | 5/2018 | McHugo |
| 2018/0133012 A1 | 5/2018 | Nathe |
| 2018/0185184 A1 | 7/2018 | Christakis |
| 2018/0193153 A1 | 7/2018 | Brenzel et al. |
| 2018/0206983 A1 | 7/2018 | Noe |
| 2018/0256259 A1 | 9/2018 | Chambers |
| 2018/0296335 A1* | 10/2018 | Miyashiro ............ A61F 2/2418 |
| 2018/0311039 A1 | 11/2018 | Cohen |
| 2018/0325664 A1* | 11/2018 | Gonda .................. A61F 2/2409 |
| 2018/0333102 A1 | 11/2018 | De Haan et al. |
| 2018/0360602 A1 | 12/2018 | Kumar |
| 2018/0369006 A1 | 12/2018 | Zhang |
| 2019/0053898 A1 | 2/2019 | Maimon et al. |
| 2019/0099265 A1 | 4/2019 | Braido |
| 2019/0105088 A1 | 4/2019 | Peterson et al. |
| 2019/0151067 A1 | 5/2019 | Zucker |
| 2019/0201192 A1* | 7/2019 | Kruse .................. A61F 2/2454 |
| 2019/0224028 A1 | 7/2019 | Finn |
| 2019/0247189 A1* | 8/2019 | Dale ..................... A61F 2/2445 |
| 2019/0247190 A1 | 8/2019 | Nathe |
| 2019/0321530 A1 | 10/2019 | Cambronne |
| 2019/0321531 A1 | 10/2019 | Cambronne |
| 2019/0365534 A1 | 12/2019 | Kramer |
| 2019/0365538 A1* | 12/2019 | Chambers ............. A61F 2/2418 |
| 2020/0000592 A1 | 1/2020 | Lee |
| 2020/0030088 A1* | 1/2020 | Vidlund ............... A61L 33/0011 |
| 2020/0030507 A1 | 1/2020 | Higgins |
| 2020/0069423 A1* | 3/2020 | Peterson .............. A61F 2/9522 |
| 2020/0069449 A1 | 3/2020 | Diedering |
| 2020/0100897 A1* | 4/2020 | McLean ............... A61F 2/2427 |
| 2020/0113682 A1 | 4/2020 | Chang |
| 2020/0129294 A1 | 4/2020 | Hariton |

(56) References Cited

U.S. PATENT DOCUMENTS

| | | |
|---|---|---|
| 2020/0155306 A1 | 5/2020 | Bonyuet |
| 2020/0163765 A1 | 5/2020 | Christianson |
| 2020/0179111 A1 | 6/2020 | Vidlund |
| 2020/0179115 A1 | 6/2020 | Chambers |
| 2020/0188101 A1 | 6/2020 | Chambers |
| 2020/0222179 A1 | 7/2020 | Chambers |
| 2020/0253733 A1 | 8/2020 | Subramanian |
| 2020/0261219 A1 | 8/2020 | Kumar |
| 2020/0276013 A1 | 9/2020 | Chambers |
| 2020/0315678 A1 | 10/2020 | Mazzio et al. |
| 2020/0337765 A1 | 10/2020 | Smith |
| 2020/0368023 A1 | 11/2020 | Kheradvar |
| 2020/0375733 A1 | 12/2020 | Diedering |
| 2021/0236274 A1 | 8/2021 | Benson |
| 2021/0275297 A1 | 9/2021 | Berndt |
| 2021/0275301 A1 | 9/2021 | Kumar |
| 2021/0290383 A1 | 9/2021 | Chambers |
| 2022/0031451 A1 | 2/2022 | Spence |
| 2022/0338979 A1 | 10/2022 | Benichou |
| 2023/0218397 A1 | 7/2023 | Chambers et al. |

FOREIGN PATENT DOCUMENTS

| | | |
|---|---|---|
| AU | 2013201970 B2 | 3/2016 |
| CN | 2820130 Y | 9/2006 |
| CN | 100413471 C | 8/2008 |
| CN | 100444811 C | 12/2008 |
| CN | 101953723 A | 1/2011 |
| CN | 101953724 A | 1/2011 |
| CN | 101953725 A | 1/2011 |
| CN | 101953728 A | 1/2011 |
| CN | 101953729 A | 1/2011 |
| CN | 101961269 A | 2/2011 |
| CN | 101961273 A | 2/2011 |
| CN | 201870772 U | 6/2011 |
| CN | 203290964 U | 11/2013 |
| CN | 103431931 A | 12/2013 |
| CN | 203379235 U | 1/2014 |
| CN | 103598939 A | 2/2014 |
| CN | 103610520 A | 3/2014 |
| CN | 203619728 U | 6/2014 |
| CN | 203677318 U | 7/2014 |
| CN | 104287804 A | 1/2015 |
| CN | 104352261 A | 2/2015 |
| CN | 204133530 U | 2/2015 |
| CN | 204181679 U | 3/2015 |
| CN | 204246182 U | 4/2015 |
| CN | 204318826 U | 5/2015 |
| CN | 104688292 A | 6/2015 |
| CN | 102985033 B | 8/2015 |
| CN | 204581598 U | 8/2015 |
| CN | 204581599 U | 8/2015 |
| CN | 204683686 U | 10/2015 |
| CN | 105596052 A | 5/2016 |
| CN | 105615936 A | 6/2016 |
| CN | 205286438 U | 6/2016 |
| CN | 107252363 B | 4/2020 |
| CN | 106913909 B | 9/2020 |
| CN | 107007887 B | 10/2020 |
| DE | 102010021345 A1 | 11/2011 |
| EP | 2596754 A1 | 5/2013 |
| EP | 2967858 A2 | 1/2016 |
| EP | 2982336 A1 | 2/2016 |
| EP | 2967845 B1 | 8/2018 |
| EP | 2950752 B1 | 7/2022 |
| JP | 2016531722 A | 10/2016 |
| WO | WO1995016476 A1 | 6/1995 |
| WO | WO2009127973 A2 | 10/2009 |
| WO | WO2014210299 A1 | 12/2014 |
| WO | WO2015004173 A1 | 1/2015 |
| WO | WO2016100806 A1 | 6/2016 |
| WO | WO2019/006387 | 1/2019 |

OTHER PUBLICATIONS

The Alta Valve™. Attributes, Challenges, and Future Programs, Dr. Philippe Genereux, MD, Jun. 22, 2018.

4C Medical's AltaValve: The First-in-Human Experience, Josep Rodes-Cabau, MD, Sep. 21, 2018.

Ferreira-Neto et al., "Transcatheter Mitral Valve Replacement With a New Supra-Annular Valve-First-in-Human Experience with the AltaValve System," https://doi.org/10.1016/j.jcin.2018.10.046, By The American College of Cardiology Foundation Published by Elsevier, Jan. 28, 2019.

Goel et al., "Transcatheter Mitral Valve Therapy with Novel Supra-Annular Alta Valve," https://doi.org/10.1016/j.jaccas.2019.10.034, Published by Elsevier on behalf of The American College of Cardiology Foundation, Dec. 18, 2019.

Hatamifar et al., "MRI Evaluation of an Atrial-Anchored Transcatheter Mitral Valve Replacement Implant," https://www.ajronline.org/doi/10.2214/AJR.19.22206 American Roentgen Ray Society, Jan. 15, 2020.

Alperi et al., "Device profile of the AltaValve System for Transcatheter Mitral Valve Replacement: Overview of its safety and Efficacy," https://doi.org/10.1080/17434440.2020.1781616, Informa UK Limited, Jun. 25, 2020.

International Search Report and Written Opinion in Application PCT/US2021/015387, dated Jun. 3, 2021.

Extended European Search Report in Application No. 21746955.0, dated Jan. 15, 2024.

\* cited by examiner

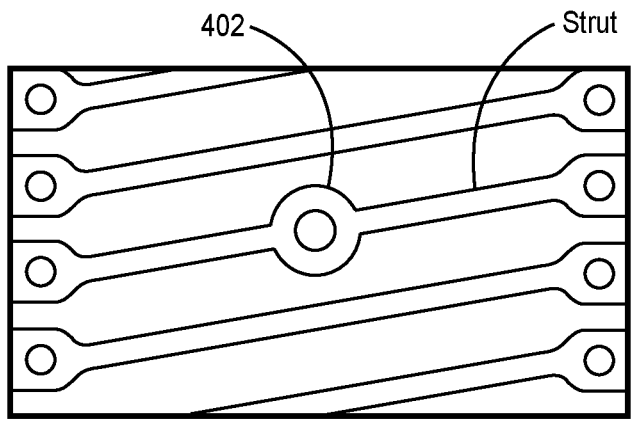
FIG. 4
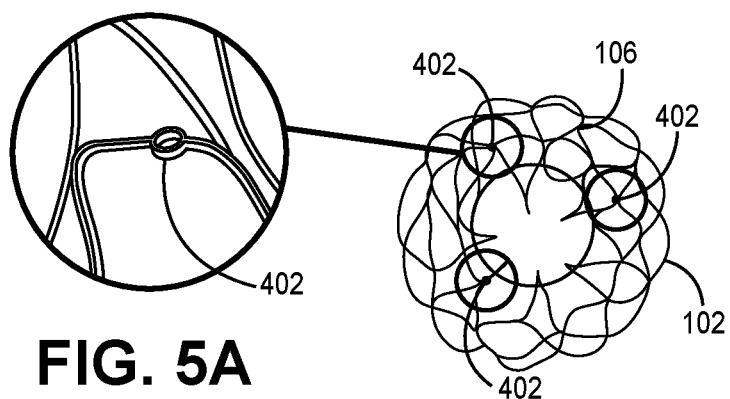
FIG. 5A  FIG. 5B

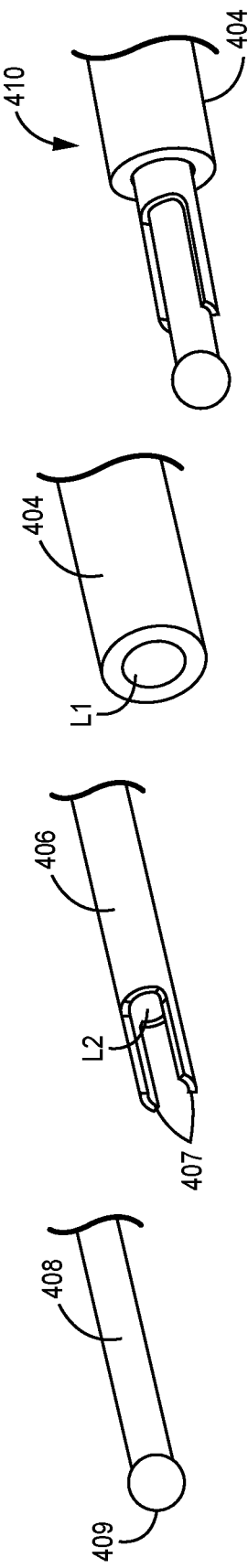
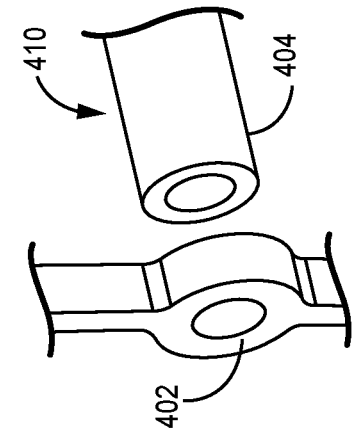
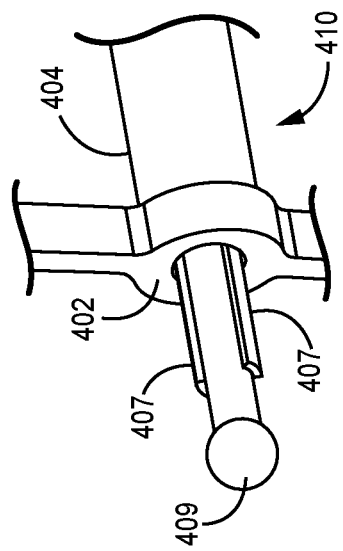
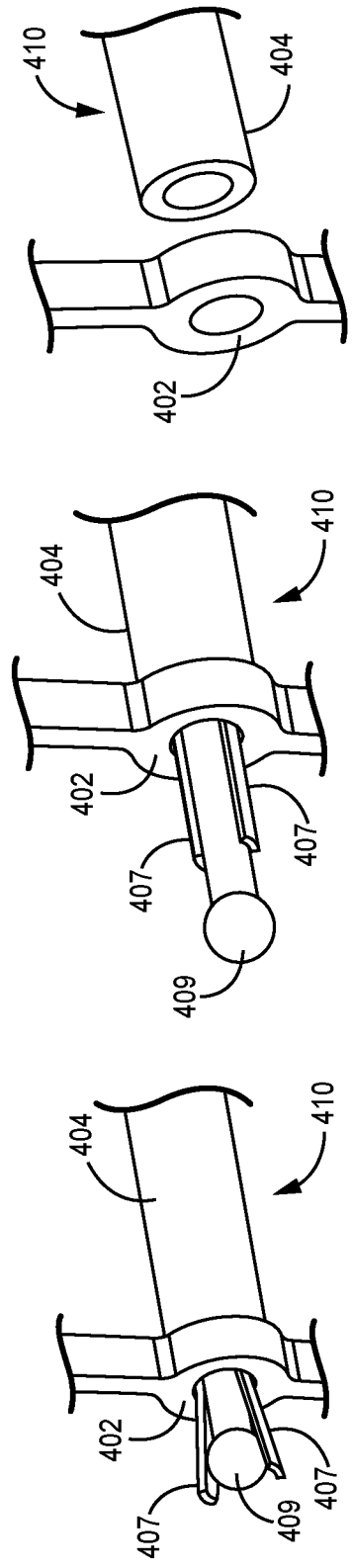
FIG. 6A  FIG. 6B  FIG. 6C  FIG. 6D
FIG. 7A  FIG. 7B  FIG. 7C

PROSTHETIC HEART VALVE DELIVERY SYSTEM: BALL-SLIDE ATTACHMENT

CROSS-REFERENCE TO RELATED APPLICATIONS

This application claims the benefit of U.S. Provisional Application No. 62/968,216, filed Jan. 31, 2020 and entitled PROSTHETIC HEART VALVE DELIVERY SYSTEM: BALL SLIDE ATTACHMENT, the entirety of which is hereby incorporated by reference.

STATEMENT REGARDING FEDERALLY SPONSORED RESEARCH OR DEVELOPMENT

Not Applicable

BACKGROUND OF THE INVENTION

Field of the Invention

The invention relates to devices and methods for implanting devices within a heart chamber.

Description of the Related Art

Stents in general, and prosthetic cardiac valve and left atrial appendage occluding devices specifically, are well known in the art. The native heart valves, e.g., aortic, pulmonary, tricuspid and mitral valves, are critical in assuring the forward-only flow of an adequate supply of blood through the cardiovascular system. These heart valves may lose functionality as a result of, inter alia, congenital, inflammatory, infectious diseases or conditions. Early interventions repaired or replaced the dysfunctional valve(s) during open heart surgery. More recently, besides the open heart surgical approach discussed above, gaining access to the valve of interest may be achieved percutaneously via one of at least the following known access routes: transapical; transfemoral; transatrial; and transseptal delivery techniques, collectively transcatheter techniques.

Generally, in a transcatheter technique, the prosthetic valve is mounted within a stented frame that is capable of achieving collapsed and expanded states. The device is collapsed and advanced through a sheath or delivery catheter positioned in a blood vessel of the patient until reaching the implantation site. The stented frame is generally released from the catheter or sheath and, by a variety of means, expanded with the valve to the expanded functional size and orientation within the heart. One of the key issues is ease of delivery of the prosthetic valve, including the stent frame and valve in all access routes, including but not limited to transapical delivery. More specifically, it would be advantageous to have an improved delivery system for attaching, loading, translating, delivering, repositioning and resheathing and deploying an expandable stent to, and within, the subject heart chamber. The present invention addresses these, inter alia, issues.

DESCRIPTION OF THE RELATED ART

The human heart comprises four chambers and four heart valves that assist in the forward (antegrade) flow of blood through the heart. The chambers include the left atrium, left ventricle, right atrium and right ventricle. The four heart valves include the mitral valve, the tricuspid valve, the aortic valve and the pulmonary valve. See generally FIG. 1.

The mitral valve is located between the left atrium and left ventricle and helps control the flow of blood from the left atrium to the left ventricle by acting as a one-way valve to prevent backflow into the left atrium. Similarly, the tricuspid valve is located between the right atrium and the right ventricle, while the aortic valve and the pulmonary valve are semilunar valves located in arteries flowing blood away from the heart. The valves are all one-way valves, with leaflets that open to allow forward (antegrade) blood flow. The normally functioning valve leaflets close under the pressure exerted by reverse blood to prevent backflow (retrograde) of the blood into the chamber it just flowed out of. For example, the mitral valve when working properly provides a one-way valving between the left atrium and the left ventricle, opening to allow antegrade flow from the left atrium to the left ventricle and closing to prevent retrograde flow from the left ventricle into the left atrium. This retrograde flow, when present, is known as mitral regurgitation or mitral valve regurgitation.

Native heart valves may be, or become, dysfunctional for a variety of reasons and/or conditions including but not limited to disease, trauma, congenital malformations, and aging. These types of conditions may cause the valve structure to fail to close properly resulting in regurgitant retrograde flow of blood from the left ventricle to the left atrium in the case of a mitral valve failure.

Mitral valve regurgitation is a specific problem resulting from a dysfunctional mitral valve that allows at least some retrograde blood flow back into the left atrium from the right atrium. In some cases, the dysfunction results from mitral valve leaflet(s) that prolapse up into the left atrial chamber, i.e., above the upper surface of the annulus instead of connecting or coapting to block retrograde flow. This backflow of blood places a burden on the left ventricle with a volume load that may lead to a series of left ventricular compensatory adaptations and adjustments, including remodeling of the ventricular chamber size and shape, that vary considerably during the prolonged clinical course of mitral regurgitation.

Regurgitation can be a problem with native heart valves generally, including tricuspid, aortic and pulmonary valves as well as mitral valves.

Native heart valves generally, e.g., mitral valves, therefore, may require functional repair and/or assistance, including a partial or complete replacement. Such intervention may take several forms including open heart surgery and open heart implantation of a replacement heart valve. See e.g., U.S. Pat. No. 4,106,129 (Carpentier), for a procedure that is highly invasive, fraught with patient risks, and requiring not only an extended hospitalization but also a highly painful recovery period.

Less invasive methods and devices for replacing a dysfunctional heart valve are also known and involve percutaneous access and catheter-facilitated delivery of the replacement valve. Most of these solutions involve a replacement heart valve attached to a structural support such as a stent, commonly known in the art, or other form of wire network designed to expand upon release from a delivery catheter. See, e.g., U.S. Pat. No. 3,657,744 (Ersek); U.S. Pat. No. 5,411,552 (Andersen). The self-expansion variants of the supporting stent assist in positioning the valve, and holding the expanded device in position, within the subject heart chamber or vessel. This self-expanded form also presents problems when, as is often the case, the device is not properly positioned in the first positioning attempt and, therefore, must be recaptured and positionally adjusted. This recapturing process in the case of a fully, or even partially, expanded device requires re-collapsing the device to a point that allows the operator to retract the collapsed device back into a delivery sheath or catheter, adjust the inbound position for the device and then re-expand to the proper position by redeploying the positionally-adjusted device distally out of the delivery sheath or catheter. Collapsing the already expanded device is difficult because the expanded stent or wire network is generally designed to achieve the expanded state which also resists contractive or collapsing forces.

Besides the open heart surgical approach discussed above, gaining access to the valve of interest is achieved percutaneously via one of at least the following known access routes: transapical; transfemoral; transatrial; transaortic; and transseptal delivery techniques.

Generally, the art is focused on systems and methods that, using one of the above-described known access routes, allow a partial delivery of the collapsed valve device, wherein one end of the device is released from a delivery sheath or catheter and expanded for an initial positioning followed by full release and expansion when proper positioning is achieved. See. e.g., U.S. Pat. No. 8,852,271 (Murray, III); U.S. Pat. No. 8,747,459 (Nguyen); U.S. Pat. No. 8,814,931 (Wang); U.S. Pat. No. 9,402,720 (Richter); U.S. Pat. No. 8,986,372 (Murray, III); and U.S. Pat. No. 9,277,991 (Salahieh); and U.S. Pat. Pub. Nos. 2015/0272731 (Racchini); and 2016/0235531 (Ciobanu).

In addition, known "replacement" prosthetic heart valves are intended for full replacement of the native heart valve. Therefore, these replacement heart valves physically engage tissue within the annular throat, i.e., below the annular plane and upper annular surface, and/or valve leaflets, thereby eliminating all remaining functionality of the native valve and making the patient completely reliant on the replacement valve. Generally speaking, it is a preferred solution that maintains and/or retains the native function of a heart valve, thus supplementation of the valve is preferred rather than full replacement. Obviously, there will be cases when native valve has either lost virtually complete functionality before the interventional implantation procedure, or the native valve continues to lose functionality after the implantation procedure. The preferred solution is delivery and implantation of a valve device that will function both as an adjunctive and/or supplementary functional valve as well as be fully capable of replacing the native function of a valve that has lost, or will lose, most or all of its functionality. However, the inventive solutions described infra will apply generally to all types and forms of heart valve devices, unless otherwise specified. The present disclosure also applies, as the skilled artisan will recognize, to stents generally.

Further, known solutions for, e.g., the mitral valve replacement systems, devices and methods require 2-chamber solutions, i.e., there is involvement and engagement of the implanted replacement valve device in the left atrium and the left ventricle. Generally, these solutions include a radially expanding stent in the left atrium, with anchoring or tethering (disposed downward through the native annulus or annular throat) connected from the stent device down through the annular throat, with the sub-annular surface within the left ventricle, the left ventricular chordae tendineae and even into the left ventricle wall surface(s). See. e.g., the MitraClip® marketed by the Abbott Group and currently the only US approved repair device. With the MitraClip® a catheter containing the MitraClip® is inserted into the femoral vein. The device enters the heart through the inferior vena cava to the right atrium and delivered transseptally. The MitraClip® passes through the annulus into the left ventricle and sits below the leaflets, clipping the leaflets to decrease regurgitation.

Such 2-chamber and native annulus solutions are unnecessary bulky and therefore more difficult to deliver and to position/recapture/reposition from a strictly structural perspective. Further, the 2-chamber solutions present difficulties in terms of making the ventricular anchoring and/or tethering connections required to hold position. Moreover, these solutions interfere with the native valve functionality as described above because the device portions that are disposed within the left ventricle must be routed through the native annulus and/or annular throat and native mitral valve, thereby disrupting any remaining coaptation capability of the native leaflets. In addition, the 2-chamber solutions generally require an invasive anchoring of some of the native tissue, resulting in unnecessary trauma and potential complication.

It will be further recognized that the 2-chamber mitral valve solutions require sub-annular and/or ventricular engagement with anchors, tethers and the like precisely because the atrial portion of the device fails to adequately anchor itself to the atrial chamber and/or upper portion of the annulus. Again, some of the embodiments, or portions thereof, described herein are readily applicable to single or 2-chamber solutions, unless otherwise indicated.

Finally, known prosthetic cardiac valves consist of two or three leaflets that are arranged to act as a one-way valve, permitting fluid flow therethrough in the antegrade direction while preventing retrograde flow. The native mitral valve is located retrosternally at the fourth costal cartilage, consisting of an anterior and posterior leaflet, chordae tendinae, papillary muscles, ventricular wall and annulus connected to the atria. Each native leaflet is supported by chordae tendinae that are attached to papillary muscles which become taut with each ventricular contraction preserving valvular competence. Both the anterior and posterior leaflets of the native valve are attached via primary, secondary and tertiary chordae to both the antero-lateral and posterio-medial papillary muscles. A disruption in either papillary muscle in the setting of myocardial injury, can result in dysfunction of either the anterior or posterior leaflet of the mitral valve. Other mechanisms may result in failure of one, or both of the native mitral leaflets. In the case of a single mitral valve leaflet failure, the regurgitation may take the form of a non-central, eccentric jet of blood back into the left atrium. Other leaflet failures may comprise a more centralized regurgitation jet. Known prosthetic valve replacements generally comprise leaflets which are arranged to mimic the native valve structure, which may over time become susceptible to similar regurgitation outcomes.

The applications for collapsible and expandable stents are not limited to prosthetic heart valve implants. Vascular stents are commonly used and are generally collapsible to facilitate delivery through the lumen of a delivery catheter to the working site where the stent is translated out of the lumen of the catheter and it is expanded, either by a self-expanding means or through an expanding mechanism such as, inter alia, an expandable balloon.

As discussed above, known delivery methods and devices comprise expandable prosthetic valve stents and vascular stents that are collapsed during delivery via a delivery catheter. Some issues with known systems, devices and methods include ease of attaching an operator-manipulatable tether(s) to the stent for: loading and/or collapsing the expandable stent into a delivery catheter or sheath, translating the collapsed stent along the delivery catheter or sheath, delivering the expandable stent into the subject heart chamber, repositioning the expandable stent as necessary within the subject heart chamber, recapturing or resheathing the expandable stent within the delivery catheter or sheath if needed, and deploying the expandable stent to, and within, the subject heart chamber.

BRIEF SUMMARY OF THE INVENTION

Systems, devices and methods for attaching an operator-manipulatable tether(s) to the stent for: loading and/or collapsing the expandable stent into a delivery catheter or sheath, translating the collapsed stent along the delivery catheter or sheath, delivering the expandable stent into the subject heart chamber, repositioning the expandable stent as necessary within the subject heart chamber, recapturing or resheathing the expandable stent within the delivery catheter or sheath if needed, and deploying the expandable stent to, and within, the subject heart chamber. The delivery system embodiments described herein apply to single chamber prosthetic heart valves as well as prosthetic heart valves that require anchoring outside of a single chamber.

BRIEF DESCRIPTION OF THE SEVERAL VIEWS OF THE DRAWINGS

FIG. 4 illustrates one embodiment of an attachment feature defined in an exemplary stent.

FIG. 5A illustrates one embodiment of an attachment feature defined in a transition section of the exemplary stent of FIG. 2.

FIG. 5B illustrates one embodiment comprising three attachment features defined in a transition section of the exemplary stent of FIG. 2.

FIG. 6A illustrates one embodiment of a wire with distal ball.

FIG. 6B illustrates one embodiment of a notched tube for slidingly receiving the wire with distal ball of FIG. 6A.

FIG. 6C illustrates one embodiment of an outer tube for receiving the notched tube of FIG. 6B.

FIG. 6D illustrates one embodiment of an assembled tether comprising the wire with distal ball, notched tube and outer tube of FIGS. 6A-6C.

FIG. 7A illustrates one embodiment of the assembled tether with the ball in a partially retracted position.

FIG. 7B illustrates one embodiment of the assembled tether in a release position.

FIG. 7C illustrates one embodiment of the assembled tether in a fully retracted position.

DETAILED DESCRIPTION OF THE INVENTION

Generally, various embodiments of the present invention are directed to devices and methods for attaching an operator-manipulatable tether(s) to the stent for: loading and/or collapsing the expandable stent into a delivery catheter or sheath, translating the collapsed stent along the delivery catheter or sheath, delivering the expandable stent into the subject heart chamber, repositioning the expandable stent as necessary within the subject heart chamber, recapturing or resheathing the expandable stent within the delivery catheter or sheath if needed, and deploying the expandable stent to, and within, the subject heart chamber.

The support structure or stent has multiple functions to aid with the treatment of cardiac valve regurgitation (mitral or tricuspid). These functions include its function as a scaffold for the functioning prosthetic valve, apposition to the atrial anatomy, optimized radial force for compliance with atrial distension, ability to load and deploy from a minimally invasive delivery system, and geometry to support with mitigating against paravalvular leak (PVL). The design features of the stent are adapted to meet one or more of the functions identified above. Specific design features and attributes for exemplary stents are discussed in detail below to assist in understanding of the utility of the funneling loading device and related methods. As the skilled artisan will recognize, the invention is not limited to prosthetic heart valves comprising stent support structures but may also be applied to collapsible and expandable stents such as commonly used for intravascular procedures. In addition, the skilled artisan will recognize the utility of the disclosed inventions for use in implanting certain exemplary embodiment stent design concepts that are intended to support minimally invasive procedures for the treatment of valvular regurgitation or other dysfunction in at least mitral, tricuspid, and aortic valves.

The stents may be self-expandable (e.g. nitinol or similar materials) or balloon expandable (e.g. cobalt chromium or similar materials). The stents are typically made of cells that may be open celled diamond like structures or continuous structures that have a working cell element. The stents may also be constructed using tubing, wires, braids or similar structures. Exemplary stent transition sections are described below.

Figure 1:
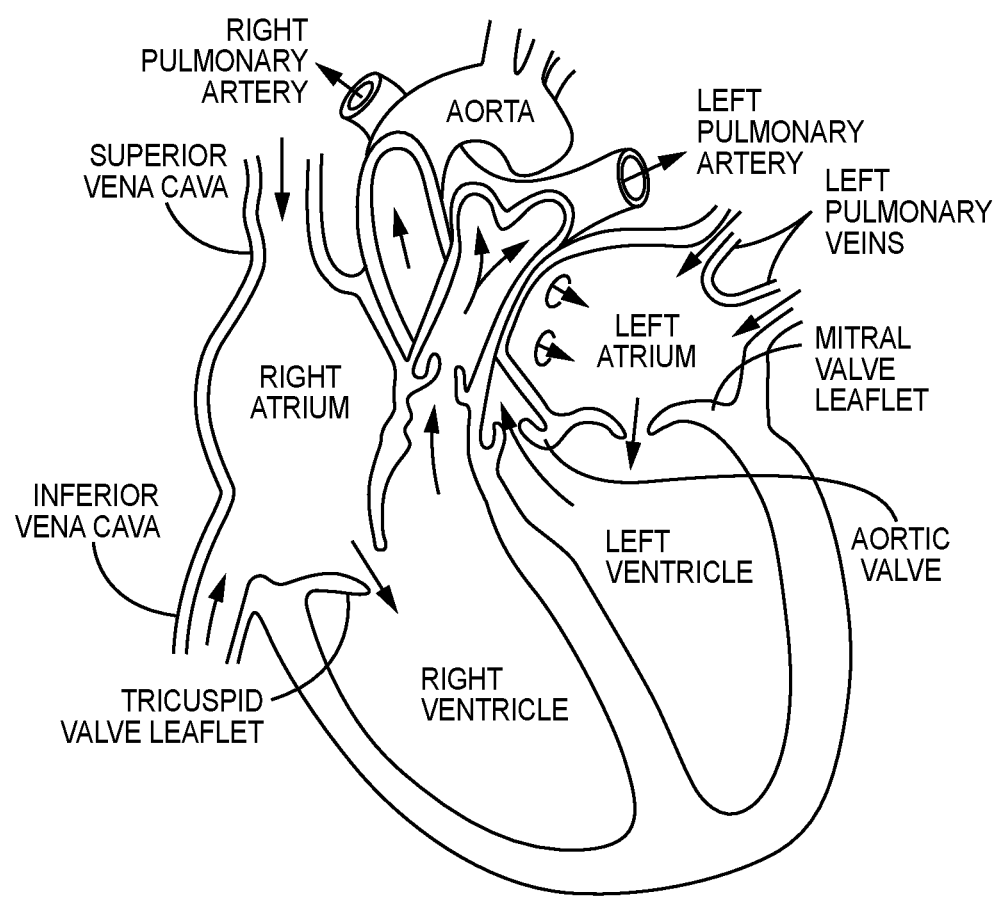
FIG. 1 illustrates certain features of the heart in cross-section.
Figure 2:
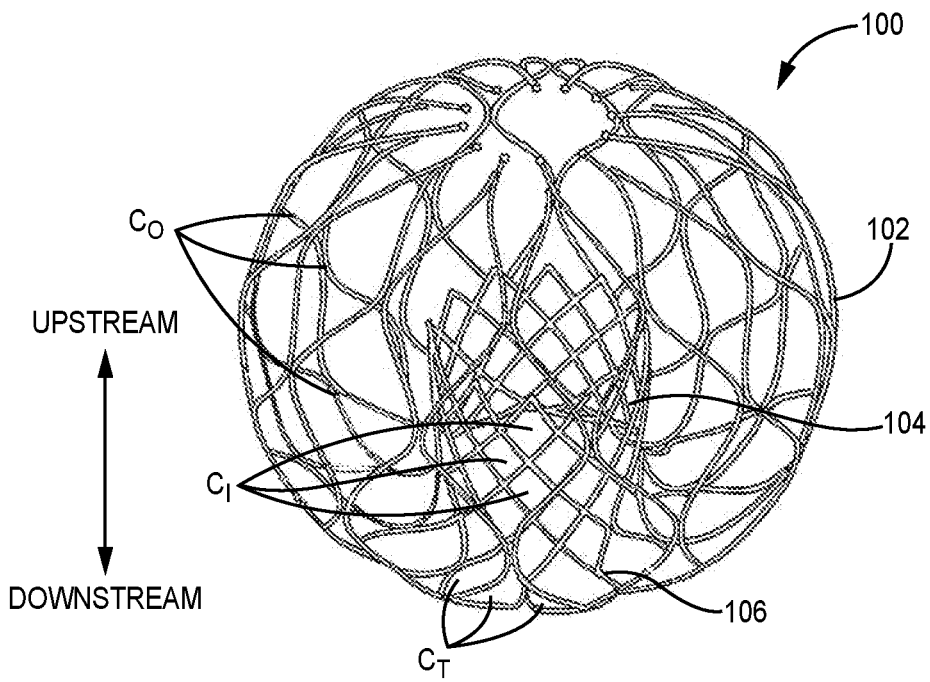
FIG. 2 illustrates a perspective view of an exemplary stent.
Figure 3A:
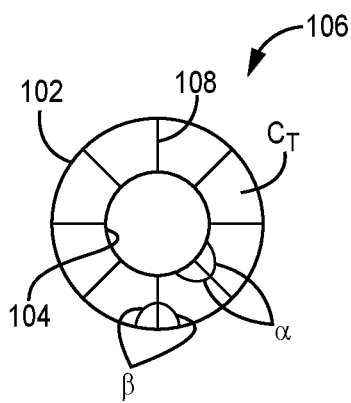
FIG. 3A illustrates a bottom view of one embodiment of a transition section of the exemplary stent of FIG. 2.
Figure 3B:
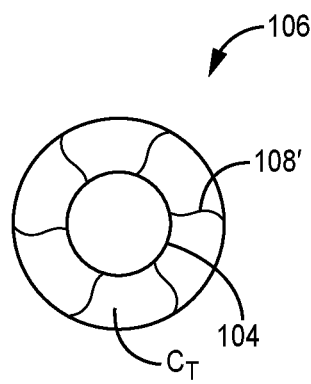
FIG. 3B illustrates a bottom view of one embodiment of a transition section of the exemplary stent of FIG. 2.
Figure 3C:
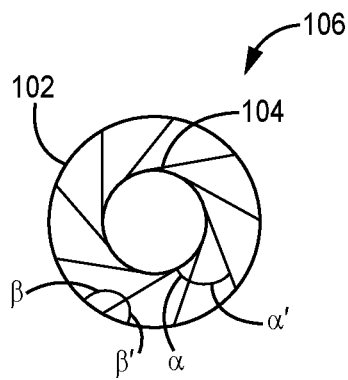
FIG. 3C illustrates a bottom view of one embodiment of a transition section of the exemplary stent of FIG. 2.

With reference now to FIGS. 2-3C, one embodiment of an exemplary expandable stent 100 for use with the present invention comprises an outer section 102—that may generally be circular though need not be a perfectly round circular structure when fully and/or partially expanded—and an inner valve support section 104—which may be cylindrical but need not be a constant diameter cylinder and is adapted to support and retain prosthetic valve leaflets (not shown in FIG. 2) within the inner valve support section 104, most preferably at a point that located above the native annulus. e.g., the mitral valve annulus, though other attachment points for the prosthetic leaflets are within the scope of the present invention. Further, as discussed above, the stent 100 may be configured to supplement and/or replace the function of the tricuspid valve. A preferred construction comprises the prosthetic leaflets disposed above the native leaflets, wherein the prosthetic leaflets are attached and spaced sufficiently away from (above) the native leaflets so as to not physically interfere or interact with the native leaflets. However, certain embodiments contemplate some interaction with the native leaflets.

Individual cells $C_O$ forming the outer section 102 of stent 100 are visible in FIG. 2 as open cell regions defined by the material used to form the exemplary expandable stent 100.

Individual cells $C_I$ forming the inner valve support section 104 are also illustrated as open cells regions formed within an inner region R defined by outer section 102, wherein the inner valve support section extends radially upward into the inner region R. As shown, individual cells $C_I$ are of a different size, and may comprise a different shape, than that of individual cells $C_O$.

The region of stent 100 that facilitates the radially inward transition of the stent 100 from the outer section 102 to the inner section 104 of the stent 100 is the transition section or cell region 106. Transition cell region 106 may comprise cells $C_T$ that may comprise a different size and/or shape that either the outer section cells $C_O$ and/or the inner section cells $C_I$. The outer and/or inner regions 102, 104, and/or transition cell region 106 of the stent 100 may be constructed from one continuous structure or may combine two or more structures to achieve intended design goals. Transition cell region 106 comprises generally a radially upward turn to allow the inner valve support section 104 to reside within the inner region 102 as shown in FIG. 2. In some embodiments, the lower portion of inner valve support section 104, that is the portion of the inner valve support section 104 that is in connection with the cells $C_T$ of transition cell region 106 may also comprise a curving shape to facilitate and/or complete the radially upward turn into the inner region 102.

The geometry and/or shape of the transition cells $C_T$ may be substantially straight segments when expanded as in FIG. 3A below or may, as shown in FIG. 3B, incorporate an offset or a twist in the stent cell pattern when expanded to allow for a controlled compression of the stent. Exemplary cross-sectional geometry of the transition cell region 106 viewed from the bottom of stent 100 is represented schematically in FIGS. 3A and 3B.

This transition cell region 106 of the stent 100 may be a strut, completed cell section or a partial cell section. The transition cell region 106 may have any number of struts (minimum of 3) or cell sections as generally required to meet design needs. Transition cells $C_T$ or struts may be evenly spaced and formed by substantially straight and equally spaced apart struts 108 as shown in FIG. 3A, that extend away from the inner valve support section 104 with equal angles α on both sides of the strut 108 and equal angles β on both sides of strut 108 with respect to its intersection or integration with outer support section 102.

In one embodiment, the struts 108 of transition section 106 may be straight as in FIG. 3A, but with non-equal angles relative to the inner valve support section 104 and outer support section 102 as shown in FIG. 3C. There, the straight struts 108 are slanted so that a smaller angle α and a larger angle α' are provided relative to the inner valve support section 104. Similarly, a smaller angle β' and a larger angle β are provided relative to the outer support section 102. This allows a compressed nesting of the slanted struts 108 of transition section 106.

In another preferred embodiment, the transition cell region 106 may comprise transition cell struts 108' that comprise transition cells $C_T$ that are formed by struts 108' having an offset, i.e., not straight, are twisted and/or curvilinear. The degree of offset and/or twist and/or curvature of the struts 108', and therefore the size and/or shape of the resultant expanded cells $C_T$ may be varied dependent on the number of cells/struts in the transition cell region 106, packing density when the stent is collapsed, and stress/strain distribution limitations of the transition cell region 106.

Turning now to FIG. 4, an attachment feature 402 is defined along one of the struts 108 as described above in FIGS. 2-3B, preferably within the transition cell region 106 of the expandable stent 102. However, the skilled artisan will recognize that attachment feature 402 may also be defined along strut(s) that are not within the transition cell region 106. In addition, the attachment feature 402 is shown as circular, but other shapes are certainly possible and within the scope of the present invention. In addition, attachment feature 402 may be defined on a strut of a stent frame that is on a downstream (of the normal blood flow within the prosthetic heart valve) side of the stent frame when implanted. Alternatively, attachment feature 402 may be defined on the lowermost downstream strut of the prosthetic heart valve frame.

FIG. 5A shows an exemplary circular attachment feature 402 disposed and defined along a stent strut and FIG. 5B illustrates the locations around the transition cell region 106 of exemplary expandable stent 102 for three (3) of the attachment features 402. As shown, there is a substantially equal spacing or separation between adjacent attachment features 402 along and/or around the transition cell region 106. The skilled artisan will recognize the non-equal spacings or separations between the locations of the attachment features 402 may also be employed. In addition, at least one attachment feature 402 may be used. It is preferable to have at least two, and more preferable to have at least three, attachment features 402 defined as described herein.

Turning now to FIGS. 6A-7A, one embodiment of a tether assembly 410 that is operationally connected at a proximal end to an operational handle, as will be discussed further, is illustrated. Tether assembly 410 further comprises an outer tube 404, a notched tube 406 and a wire with distal enlarged element 408, wherein tether assembly comprises a length that enables proximal connection with handle H and sufficient extension length from the distal end of a delivery catheter or sheath to facilitate, inter alia, translation and deployment of the subject prosthetic heart valve as will be further discussed herein. The wire distal enlarged element 408 is not restricted to a wire and may also include equivalent structures such as but not limited to a tube, a rod that may be hollow or solid, and the like.

Outer tube 404 is provided having a lumen L1 therethrough. Notched tube 406 is sized to be slidingly received within lumen L1 and comprises distal flexible tabs 407 extending distally from notched tube lumen L2, as shown.

Wire with distal enlarged element 408, wherein the enlarged distal element 409 is shown as a ball, is adapted to be slidingly received within lumen L2, creating a nested arrangement as shown in FIG. 6D for the tether assembly 410.

FIGS. 7A-7C illustrate the operation and relationship of the components of tether assembly 410 during certain steps of the prosthetic heart valve loading, translating, repositioning, recapture, deployment and release during the implanting process.

FIG. 7A shows the distal enlarged element 409 of the wire with distal enlarged distal element 408 pulled proximally back into the distal flexible tabs 407 of the notched tube 406, deforming the tabs 407 to create a compression or friction fit therein. In addition, the distance between the tabs 407 when deformed as shown is greater than the distance therebetween when the ball 409 is not interposed between the tabs 407. This arrangement enables the enlarged distal element, as shown a ball, 409, having a diameter that is smaller than a smallest diameter of the attachment feature 402, and the distal flexible tabs 407, also having a maximum non-deformed length between the tabs 407 that is smaller than a smallest diameter of the attachment feature 402, to be inserted through the attachment feature. The insertion position is as shown in FIG. 6D, with distal enlarged element 409, shown as a ball, positioned distal to the distal flexible tabs 407. When the distal enlarged element 409 and distal flexible tabs 407 are inserted through attachment feature 402, the operator may then retract proximally the wire with enlarged distal element 408 as shown in FIG. 7A to engage and deform the distal flexible table 407 with distal enlarged element 409, causing the distance between the tabs 407 to increase to a length that is now greater than the diameter of the attachment feature, thereby attaching the tether assembly 410 to the stent 102, preferably at the transition section as discussed above. This process step is repeated for each of the at least one tether assembly 410 to attach the tether assembly(ies) 410 to the stent 102.

The skilled artisan will appreciate that, though a preferred embodiment comprises a ball shaped distal enlarged element 409 and a circular attachment feature 402, other shapes may be used for the ball-shaped distal enlarged element 409 and/or attachment feature 402. Some of these shapes may be complementary, e.g., a square element substituting for the distal ball-shaped distal enlarged element 409 and a square attachment feature 402. However, complementary features are not required so long as the distal element, e.g. the illustrated ball 409, fits through the attachment feature 402 and can be pulled distally to deform the flexible distal tabs 407 to achieve attachment.

The skilled artisan will also appreciate that a paravalvular leakage mitigation skirt or fabric may cover at least part of the expandable stent 102, including but not limited to the transition cell region. In such a case, the tether assembly 410 may extend through the skirt or fabric to reach and attach to, and release from, the attachment feature 402.

Figure 10C:
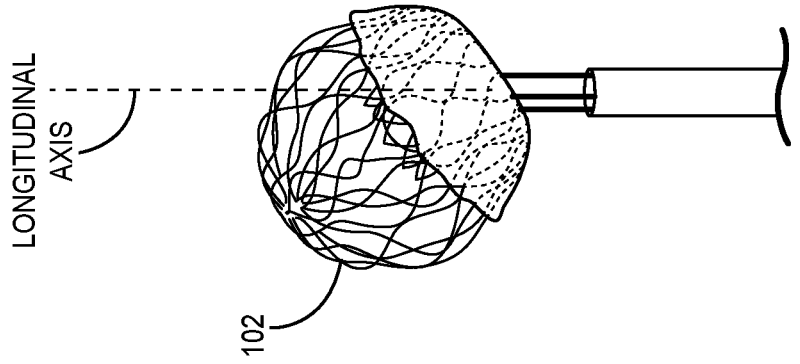
FIG. 10C illustrates three exemplary tether assemblies attached to three attachment features of an exemplary stent frame with displacement in a second direction relative to a longitudinal axis.
Figure 10B:
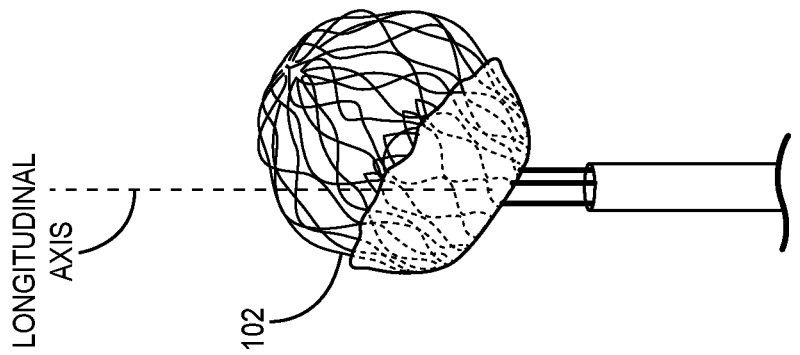
FIG. 10B illustrates three exemplary tether assemblies attached to three attachment features of an exemplary stent frame with displacement in a first direction relative to a longitudinal axis.
Figure 10A:
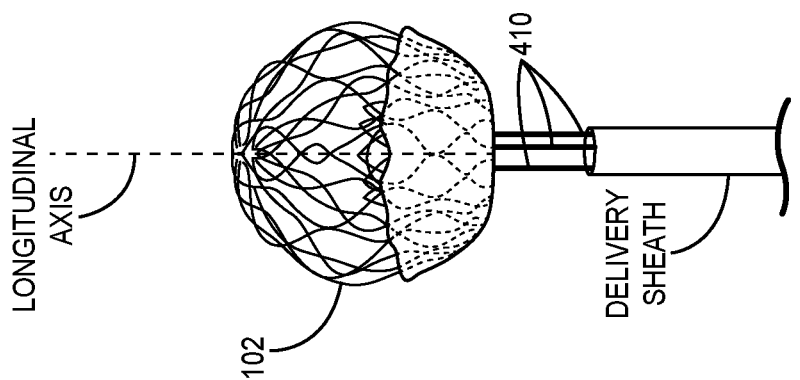
FIG. 10A illustrates three exemplary tether assemblies attached to three attachment features of an exemplary stent frame, without displacement from a longitudinal axis.
Figure 11A:
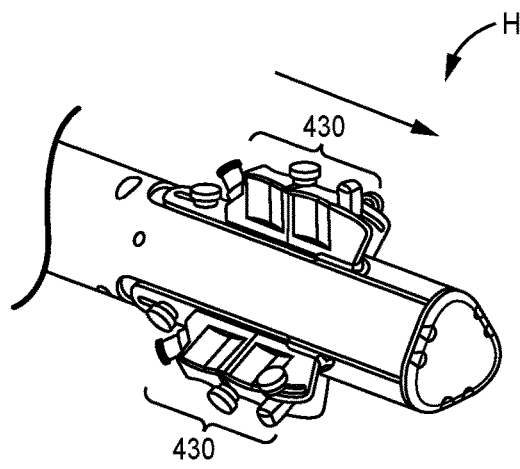
FIG. 11A illustrates an exemplary handle and mechanism for adjusting (decreasing) the extension of each tether assembly distally from the distal end of the delivery catheter or sheath.
Figure 11B:
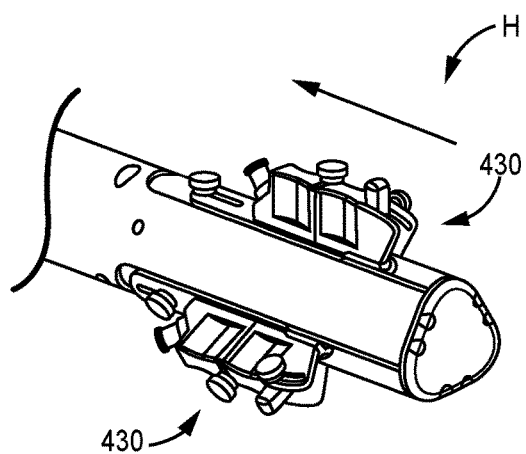
FIG. 11B illustrates an exemplary handle and mechanism for adjusting (increasing) the extension of each tether assembly distally from the distal end of the delivery catheter or sheath.

Thus attached to the stent frame, the tether assembly (ies) 410 may be used to collapse the self-expanding stent frame 102 into the proximal end of the lumen of a delivery catheter or sheath and assist in translating the collapsed stent frame 102 distally through the delivery catheter or sheath to the distal end of the delivery catheter of sheath which is prepositioned at the heart chamber of interest. At this point, the collapsed stent frame 102 is at least partially released from the delivery catheter or sheath and begins to self-expand. The attached tether assembly(ies) 410 may be used to assist in this process by manipulating the tether assembly(ies) 410 to move the at least partially expanded stent frame 102 into proper position within the subject heart chamber. In certain cases, it may be advantageous to reposition the at least partially expanded stent frame comprising a prosthetic heart valve by pulling proximally one or more of the tether assembly(ies) 410 to move the stent frame 102 in a desired direction and into a desired attitude within the heart valve, relative to anatomical landmarks. FIGS. 10A-10C illustrate one embodiment comprising three tether assemblies 410 wherein FIG. 10A is a default position and the stent frame 102 is substantially symmetrically aligned with the longitudinal axis of the delivery sheath. FIGS. 10B and 10C show the ability of pulling (or pushing) one or more tether assembly(ies) 410 to cause the connected stent frame 102 to move away from the symmetrical alignment of the longitudinal axis to take on an asymmetrical attitude to assist in positioning and deploying the stent frame 102.

FIGS. 11A and 11B, and 12A and 12B, provide embodiments of an operating handle H to which the distal end of each tether assembly 410 is connected. As indicated, the length of extension of the tether assembly 410 away from the distal end of the delivery sheath may be manipulated by moving the attached push/pull and release mechanism 430 proximally or distally at the handle H. This may be done as a combined set of tether assemblies, or individual tether assemblies 410 may be selected for selective lengthening (pushing it distally) or shortening (pulling it proximally), relative to the other tether assembly(ies) 410, and/or the components of each tether assembly 410 comprising the outer tube 404, the notched tube 406 and the wire with enlarged distal element 408 may each be pushed proximally and/or pulled distally independently. Each tether assembly 410 has its own length and release mechanism 430 attached to handle H.

Each push/pull and release mechanism 430 further comprises a lever that may be locked and unlocked and allows manipulation of the individual components of the tether assembly 410. When locked, the associated tether assembly 410 is attached to an attachment feature 402 as described above. Releasing the tether assembly 410 from the attachment feature 402 is achieved by, as in FIGS. 12A-12B, by unlocking a lever (actuating the lever as shown), and then pulling the unlocked portion of the assembly distally, i.e., pulling distally the related component of the tether assembly, i.e., the notched tube 406, the wire with enlarged distal element 408) distally and out of attached engagement with the attachment feature 402. It will be obvious now to the skilled artisan that this same mechanism 430 may be used to advance and/or retract the components of the tether assembly 410 to achieve attachment with, and/or release from, the attachment feature 402.

Figure 12A:
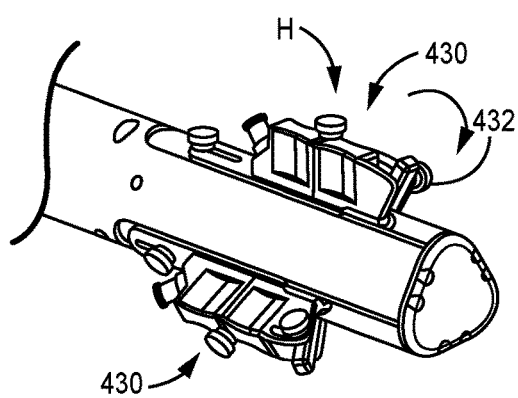
FIG. 12A illustrates an exemplary handle and mechanism for releasing one of the tether assemblies from attachment to the exemplary attachment features of the stent.
Figure 12B:
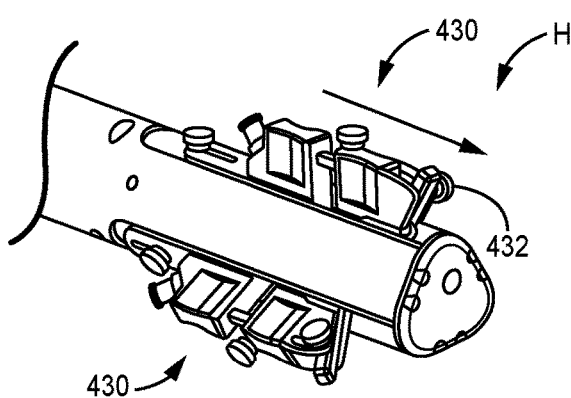
FIG. 12B illustrates an exemplary handle and mechanism for releasing one of the tether assemblies from attachment to the exemplary attachment features of the stent.

FIGS. 12A-12B provide a mechanism by which the tether assemblies 410 are individually released from the stent frame and retracted proximally as in FIGS. 7B and 7C.

In some cases, it may be advantageous to at least partially recover, resheath and/or recapture the at least partially expanded stent frame 102 by pulling it proximally into the lumen of the delivery catheter or sheath, then reinitiating release and deployment steps.

When the stent frame comprising the prosthetic heart valve is properly positioned, as shown in FIGS. 7B and 7C, the enlarged distal element 409 of the wire with enlarged distal element 408 is pushed distally away from the distal flexible tabs 407, so that the distal flexible tabs 407 return to their undeformed shape which allows the notched tube 406 and wire with distal enlarged element 408 to be withdrawn from the attachment feature 402, thereby disconnecting the tether assembly 410 from the stent frame 102. Once each provided tether assembly 410 is disconnected from the stent frame 102, the tether assembly(ies) 410 may be withdrawn from the heart chamber.

Figure 8:
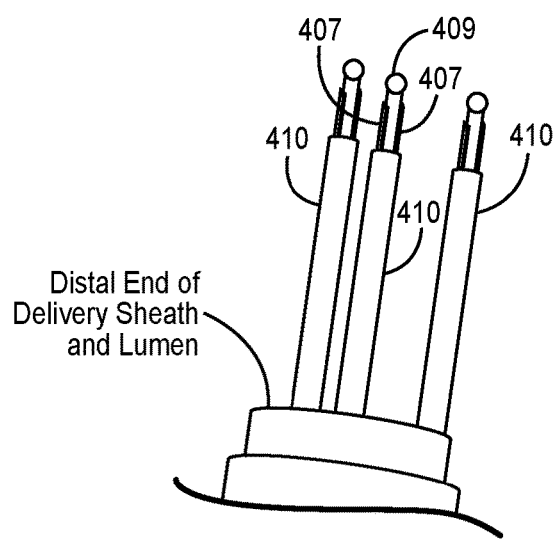
FIG. 8 illustrates one embodiment of three spaced-apart tether assemblies extending distally from a delivery catheter or sheath.
Figure 9:
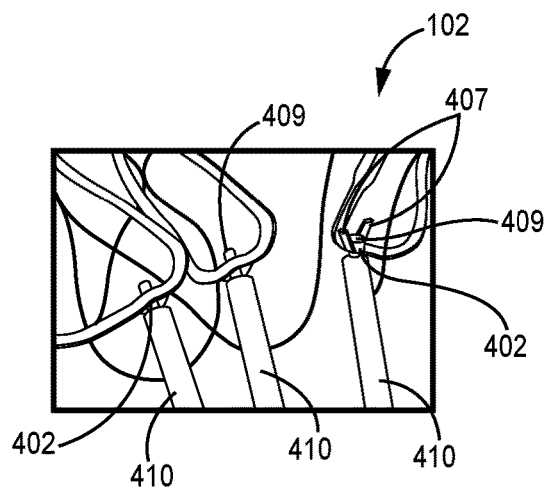
FIG. 9 illustrates one embodiment of three spaced-apart tether assemblies attached to three attachment features defined in a transition section of the exemplary stent of FIG. 2.

FIGS. 8 and 9 provide additional detail for a preferred embodiment comprising three (3) tether assemblies (410).

As discussed, a preferred access route for the disclosed delivery system comprises a transapical approach, though all other delivery access routes may be successfully navigated using the disclosed invention(s).

The description of the invention and its applications as set forth herein is illustrative and is not intended to limit the scope of the invention. Features of various embodiments may be combined with other embodiments within the contemplation of this invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

We claim:

1. Apparatus comprising:
a stent frame forming;
   an outer section defining an inner region;
   a transition section defining a downstream edge of the stent frame;
   an inner valve support section supported by the transition section and disposed within the inner region, wherein the inner valve support section defines an inner valve support that is configured to support prosthetic valve leaflets within the inner valve support; and
   wherein the outer section and transition section comprise struts that define cells of the stent frame;
one or more attachment features comprising a shape and defined on or along one or more radially inwardly turning struts of the transition section; and
one or more tether assemblies, each tether assembly comprising:
   a notched tube defining a lumen therethrough and a distal end including two flexible tabs; and
   a wire slidingly received within the lumen of the notched tube, the wire including an enlarged distal element positioned at a wire distal end;
wherein:
   each of the one or more attachment features are configured to releasably receive one of the tether assemblies;
   each of the one or more tether assemblies is configured to form, in a first arrangement, a first unlocked position and, in a second arrangement, a second locked position;
   when in the first unlocked position, the notched tube and the wire can be advanced through an opening defined by the attachment feature; and
   after being advanced through the attachment feature, the notched tube and the wire are configured to transition from the first unlocked position to the second locked position, where, in the second locked position, the flexible tabs and enlarged distal element are prevented from being withdrawn through the opening.

2. The apparatus of claim 1, further comprising the struts of the transition section adapted to turn radially inward to form the inner valve support.

3. The apparatus of claim 1, further comprising a plurality of attachment features defined on or along three struts of the transition section.

4. The apparatus of claim 3, wherein each of the plurality of attachment features are equally spaced apart from the other two attachment features around the transition section.

5. The apparatus of claim 3, wherein each of the plurality of attachment features are non-equally spaced apart from the other two attachment features around the transition section.

6. The apparatus of claim 3, further comprising three attachment features.

7. The apparatus of claim 1, wherein each of the one or more attachment features comprise a circular shape.

8. The apparatus of claim 1, wherein the stent frame is self-expandable or balloon expandable.

9. The apparatus of claim 1, wherein the outer section is circular.

10. The apparatus of claim 1, wherein the outer section is not circular.

11. The apparatus of claim 1, wherein the inner valve support comprises a cylinder.

12. The apparatus of claim 1, wherein the inner valve support comprises a non-constant diameter along a length of the inner valve support.

13. The apparatus of claim 1 further comprising the prosthetic valve leaflets, wherein the prosthetic valve leaflets are supported within the inner valve support at a location that is upstream from the transition section.

14. The apparatus of claim 1 wherein:
each tether assembly further comprises an outer tube comprising a lumen therethrough;
the notched tube and wire are slidingly received within the lumen of the outer tube; and
the two flexible tabs and enlarged distal element are configured to be extended distally from the lumen of the outer tube.

15. The apparatus of claim 1 wherein:
in the first unlocked position, the enlarged distal element is absent from between the flexible tabs; and
in the second locked position, the enlarged distal element is disposed between the flexible tabs.

* * * * *